(12) United States Patent
Zon et al.

(10) Patent No.: US 8,168,428 B2
(45) Date of Patent: May 1, 2012

(54) METHOD TO MODULATE HEMATOPOIETIC STEM CELL GROWTH

(75) Inventors: Leonard I. Zon, Wellesley, MA (US); Trista E. North, Newton Center, MA (US); Wolfram Goessling, Chestnut Hill, MA (US)

(73) Assignees: Children's Medical Center Corporation, Boston, MA (US); The General Hospital Corporation, Boston, MA (US)

( * ) Notice: Subject to any disclaimer, the term of this patent is extended or adjusted under 35 U.S.C. 154(b) by 283 days.

(21) Appl. No.: 12/294,344

(22) PCT Filed: Apr. 26, 2007

(86) PCT No.: PCT/US2007/007419
§ 371 (c)(1),
(2), (4) Date: Jul. 10, 2009

(87) PCT Pub. No.: WO2007/112084
PCT Pub. Date: Oct. 4, 2007

(65) Prior Publication Data
US 2009/0285786 A1    Nov. 19, 2009

Related U.S. Application Data

(60) Provisional application No. 60/785,968, filed on Mar. 24, 2006.

(51) Int. Cl.
*C12N 5/00* (2006.01)
*C12N 5/02* (2006.01)
(52) U.S. Cl. ........................................ 435/375; 435/377
(58) Field of Classification Search .................. 435/375, 435/377
See application file for complete search history.

(56) References Cited

U.S. PATENT DOCUMENTS

| 6,207,802 | B1 | 3/2001 | Zsebo | |
| 7,625,752 | B2 * | 12/2009 | Casper et al. | 435/377 |
| 2005/0054103 | A1 | 3/2005 | Peled et al. | |
| 2005/0074435 | A1 * | 4/2005 | Casper et al. | 424/93.7 |

FOREIGN PATENT DOCUMENTS
WO    00/50568 A2    8/2000

OTHER PUBLICATIONS

Stier et al., Notch1 activation increases hematopoietic stem cell self-renewal in vivo and favors lymphoid over myeloid lineage outcome, Blood 99(7):2369-78, 2002.*
Cohn, S.M. et al., Journal of Clinical Investigation, 99(6):1367-1379 (1997). "Crypt stem cell surivival in the mouse intestinal epithelium is regulated by prostaglandins synthesized through cyclooxygenase-1."
Feher, I. et al., Nature, 247(442):550-551 (1974). "Prostaglandin E2 as stimulator of haemopoietic stem cell proliferation."
Hanson, W.R. et al., Radiation Research, 103(2):196-203 (1985). "16 16 dimethylprostaglandin E-2 induces radioprotection in murine intestinal and hematopoietic stem cells."
Desplat et al., Experimental Hematology, 28:741-742 (2000). "Is the COX-2 effect on accelerated hematopoiesis mediated by prostaglandin E2?".
Dupuis et al., Prostaglandins & Other Lipid Mediators, 55:179-186 (1998). "Prostaglandin E2 Stimulates the Growth of Human Blood CD34+ Progenitors."
Gentile et al., Blood, 62(5):1100-1107 (1983). "In Vivo Modulation of Murine Myelopoiesis Following Intravenous Administration of Prostaglandin E2."
Bug, G. et al. "Valproic Acid Stimulates Proliferation and Self-renewal of Hematopoietic Stem Cells," Cancer Research 65(7):2537-2541 (2005).
Galloway, J.L. et al. "Ontogeny of hematopoiesis: examining the emergence of hematopoietic cells in the vertebrate embryo," Curr Top Dev Biol. 53:139-158 (2003).
Gidali, J. et al. "The Effect of E. Type Prostaglandins on the Proliferation of Haemopoietic Stem Cells In Vivo," Cell Proliferation 10(4):365-373 (1977).
Kishi, T. et al. "Bone marrow suppression induced by high dose valproic acid," Arch Dis Child 71(2):153-155 (1994).
Okunieff, P. et al. "Effects of hydralazine on in vivo tumor energy metabolism, hematopoietic radiation sensitivity, and cardiovascular parameters," International Journal of Radiation Oncology, Biology, Physics 16(5):1145-1148 (1989).
Sankaranarayanan, K. et al., "Radioprotective Effects of Prostaglandins for Chromosomal Aberrations and Cell Killing in V79 Chinese Hamster Cells Grown as Spheroids in Vitro and for Mouse Spermatogonial Stem Cells and Bone Marrow Cells in Vivo," International Journal of Radiation Biology 67(1):47-55 (1995).

* cited by examiner

*Primary Examiner* — Wu-Cheng Winston Shen
(74) *Attorney, Agent, or Firm* — David S. Resnick; Nixon Peabody LLP

(57) ABSTRACT

The present invention provides for compositions and methods for modulating hematopoietic stem cell populations by using HCS modulators, which are agents that either increase HSC numbers or decrease HSC numbers as desired by a particular indication. For example, HSC modulators found to increase HSC numbers include prostaglandin E2 (PGE2) and agents that stimulate the PGE2 pathway. Conversely, HSC modulators that prevent PGE2 synthesis decrease HSC numbers. HCS modulators may be used in vitro, in vivo, or ex vivo.

3 Claims, 24 Drawing Sheets

METHOD TO MODULATE HEMATOPOIETIC STEM CELL GROWTH

CROSS-REFERENCE TO RELATED APPLICATIONS

This application is a 35 U.S.C. §371 National Phase Entry of the co-pending International Application No. PCT/US2007/007419 filed on Mar. 26, 2007, which designates the United States, and which claims the benefit under 35 U.S.C. §119(e) of U.S. Provisional No. 60/785,968 filed on Mar. 24, 2006, the entire contents of which are incorporated herein by reference.

GOVERNMENT SUPPORT

This invention was supported by the National Institutes of Health—NIH Grant No. CA103846-02. The government of the United States has certain rights thereto.

FIELD OF THE INVENTION

The present embodiments provide for modulators that either increase or decrease hematopoeitic stem cell populations in vitro, in vivo, and ex vivo.

BACKGROUND

Stem cell research holds extraordinary potential for the development of therapies that may change the future for those suffering from diseases such as leukemia, diabetes, and anemia. Much research focuses on the exploration of stem cell biology as a key to treatments for diseases. Through an understanding of the role of stem cells in normal development, researchers seek to capture and direct the innate capabilities of stem cells to treat many conditions. Research is on-going in a number of areas simultaneously: examining the genetic and molecular triggers that drive embryonic stem cells to develop in various tissues; learning how to push those cells to divide and form specialized tissues; culturing embryonic stem cells and developing new lines to work with; searching for ways to eliminate or control Graft Vs. Host Disease by eliminating the need for donors; and generating a line of universally transplantable cells.

Hematopoietic stem cells (HSCs) are derived during embryogenesis in distinct regions where specific inductive events convert mesoderm to blood stem cells and progenitors. There remains a need to elucidate the relationships between particular biomolecules, chemical agents, and other factors in these inductive events. For example, there remains a need to identify which biomolecules or chemical agents show promise in manipulating the HSC population for a desired purpose, such as increasing a HCS population for research or therapeutics.

SUMMARY

The compositions and methods of the present embodiments provide for HCS modulators, which are agents that either increase HSC numbers or decrease HSC numbers as desired by a particular indication. For example, HSC modulators found to increase HSC numbers include prostaglandin $E_2$ (PGE2) and agents that stimulate the PGE2 pathway. Conversely, HSC modulators that prevent PGE2 synthesis decrease HSC numbers.

One embodiment provides a method for promoting hematopoietic stem cell growth in a subject, comprising administering at least one hematopoietic stem cell (HSC) modulator and a pharmaceutically acceptable carrier.

In another embodiment, the HSC modulator increases HSCs by modifying the prostaglandin pathway. A HSC modulator that enhances HCS populations by modifying the prostaglandin pathway may be at least one compound selected from the group consisting of PGE2, dmPGE2, PGI2, Linoleic Acid, 13(s)—HODE, LY171883, Mead Acid, Eicosatrienoic Acid, Epoxyeicosatrienoic Acid, ONO-259, Cay1039, a PGE2 receptor agonist, and a derivative of any of these agents. In a more particular embodiment, the HSC modulator is a PGE2 derivative selected from the group consisting of 16,16-dimethyl PGE2, 19(R)-hydroxy PGE2, 16,16-dimethyl PGE2 p-(p-acetamidobenzamido) phenyl ester, 11 deoxy-16,16-dimethyl PGE2,9-deoxy-9-methylene-16,16-dimethyl PGE2,9-deoxy-9-methylene PGE2, Butaprost, Sulprostone, PGE2 serinol amide, PGE2 methyl ester, 16-phenyl tetranor PGE2, 15(S)-15-methyl PGE2, and 15(R)-15-methyl PGE2.

In another embodiment, the HSC modulator increases HSCs by modifying the Wnt pathway. A HSC modulator that enhances HCS populations by modifying the wnt pathway may be at least compound selected from the group consisting of PGE2, dmPGE2, BIO, LiCl, and derivatives of these compounds.

In yet another embodiment, the HSC modulator increases HSCs by modifying cAMP/P13K/AKT second messenger. A HSC modulator that enhances HCS populations by modifying cAMP/P13K/AKT second messenger may be at least one compound selected from the group consisting of 8-bromo-cAMP, Forskolin, and derivatives of these agents.

In still another embodiment, the HSC modulator increases HCS populations by modifying Ca2+ second messenger. A HCS modulator that enhances HCS populations by modifying Ca2+ second messenger may be at least one agent selected from the group consisting of Bapta-AM, Fendiline, Nicardipine and derivatives of these compounds.

In another embodiment, the HSC modulator increases HSCs by modifying NO/Angiotensin signaling. A HCS modulator that enhances HCS populations by modifying NO/Angiotensin signaling may be at least one compound selected from the group consisting of L-Arg, Sodium Nitroprusside, Sodium Vanadate, Bradykinin, and derivatives thereof.

In yet another embodiment, the HSC modulator that enhances HCS populations may be at least one agent selected from the group consisting of Mebeverine, Flurandrenolide, Atenolol, Pindolol, Gaboxadol, Kynurenic Acid, Hydralazine, Thiabendazole, Bicuclline, Vesamicol, Peruvoside, Imipramine, Chlorpropamide, 1,5-Pentamethylenetetrazole, 4-Aminopyridine, Diazoxide, Benfotiamine, 12-Methoxy-dodecenoic acid, N-Formyl-Met-Leu-Phe, Gallamine, IAA 94, Chlorotrianisene, and derivatives of these compounds.

Another embodiment provides a method for promoting HSC growth by contacting a nascent stem cell population with at least one compound selected from the group consisting of PGE2, PGI2, Linoleic Acid, 13(s)—HODE, LY171883, Mead Acid, Eicosatrienoic Acid, Epoxyeicosatrienoic Acid, ONO-259, Cay1039, a PGE2 receptor agonist, of 16,16-dimethyl PGE2, 19(R)-hydroxy PGE2, 16,16-dimethyl PGE2 p-(p-acetamidobenzamido) phenyl ester, 11-deoxy-16,16-dimethyl PGE2,9-deoxy-9-methylene-16,16-dimethyl PGE2, 9-deoxy-9-methylene PGE2, Butaprost, Sulprostone, PGE2 serinol amide, PGE2 methyl ester, 16-phenyl tetranor PGE2, 15(S)-15-methyl PGE2, 15(R)-15-methyl PGE2, BIO, 8-bromo-cAMP, Forskolin, Bapta-AM, Fendiline, Nicardipine, Nifedipine, Pimozide, Strophanthidin, Lanatoside, L-Arg, Sodium Nitroprusside, Sodium Vanadate, Bradykinin, Mebeverine, Flurandrenolide, Atenolol, Pindolol, Gaboxadol, Kynurenic Acid, Hydralazine, Thiabendazole, Bicuclline, Vesamicol, Peruvoside, Imipramine, Chlorpropamide, 1,5-Pentamethylenetetrazole, 4-Aminopyridine, Diazoxide, Benfotiamine, 12-Methoxydodecenoic acid, N-Formyl-Met-Leu-Phe, Gallamine, IAA 94, Chlortrianisene, and derivatives thereof. The nascent stem cell population may be collected from peripheral blood, cord blood, chorionic villi, amniotic fluid, placental blood, or bone marrow.

Another embodiment of the present invention provides a method for promoting HSC expansion ex vivo, comprising incubating HSC in the presence of at least one HSC modulator. Another embodiment of the present invention provides a method for promoting HSC expansion ex vivo, comprising collecting HSC source sample (e.g., peripheral blood, cord blood, amniotic fluid, placental blood, bone marrow, chorionic villi) and storing it in the presence of at least one HSC modulator such as PGE2. A particular embodiment provides for a kit comprising a container suitable for HCS-source sample storage in which the container is pre-loaded with at least one HSC modulator that increases HCSs. An additional embodiment provides a kit comprising a container suitable for HCS-source sample storage and a vial containing a suitable amount of at least one HSC modulator that increases HSCs. A further embodiment of the present invention provides a method for promoting HSC expansion ex vivo, in which the nascent HSC source is contacted with PGE2, or a derivative thereof, at initial collection, during processing, at storage, upon thawing, or during transfusion.

In another embodiment of the present invention, the HSC modulator inhibits HSCs by modifying the prostaglandin pathway. A HSC modulator that inhibits HCS populations by modifying the prostaglandin pathway may be at least one compound selected from the group consisting of Indomethacin, Fenbufen, NS398, SC560, Sulindac, Suxibuzone, Aspirin, Naproxen, Ibuprofen, Celecoxib, PGJ2, Aristolochic Acid, AH6809, AH23848, and derivatives of these.

In another embodiment, the HSC modulator inhibits HSCs by modifying the Wnt pathway. A HSC modulator that inhibits HCS populations by modifying the Wnt pathway may be at least one of the agents selected from the group consisting of prostaglandin inhibitors, Kenpaullone, ValproicAcid, or a derivative thereof.

In yet another embodiment of the present invention, the HSC modulator inhibits HSCs by modifying cAMP/P13K/AKT second messenger. A HSC modulator that inhibits HCS populations by modifying the cAMP/P13K/AKT second messenger may be one or more compounds selected from the group consisting of PD98059, KT5720, H89, U0126, Wortmannin, and derivative thereof.

In another embodiment, the HSC modulator inhibits HSCs by modifying $Ca^{2+}$ second messenger. A HSC modulator that inhibits HCS populations by modifying the $Ca^{2+}$ second messenger may be at least one agent selected from the group consisting of BayK-8644, Thioridazine, and derivative of these agents.

In still another embodiment, the HSC modulator inhibits HSCs by modifying NO/Angiotensin signaling. A HSC modulator that inhibits HCS populations by modifying NO/Angiotensin signaling may be at least one compound selected from the group consisting of L-NAME, Enalapril, Captopril, AcSDKP, Losartan, AcSDKP, Losartan, Telimasartan, Histamine, Ambroxol, Chrysin, Cycloheximide, Methylene Blue, Epinephrine, Dexamethazone, Proadifen, Benzyl isothiocyanate, Ephedrine, and derivatives thereof.

In an additional embodiment of the invention, the HSC modulator that inhibits HCS populations is at least one compound selected from the group consisting of Paragyline, Propranolol, Etanidazole, Methimazole, Cinoxacin, Penicillamine, Furosemide, Eburnamininone, Aclarubicin, Warfarin, Gamma-aminobutyric Acid, Norethindrone, Lupinidine, Hydroquinidine, Todralazine, Methoxamine, Hydroxyurea, Dihydroergotamine, Antazoline, 3-Nitropropionic Acid, N-Phenylanthranilic Acid, Phenazopyridine, Dichlorokynurenic acid, 3-estradiol, L-Leu, Phenoxybenzamine, Mephentermine, Guvacine, Guaiazulene, Imidazole, Beta-Carotene, Clofibrate, and derivatives of these compounds.

Yet another embodiment provides for a method for inhibiting HSC growth in a subject, comprising administering at least one HSC modulator and a pharmaceutically acceptable carrier. In a particular embodiment, the HSC modulator is one or more of the compounds selected from the group consisting of Indomethacin, Celecoxib, Fenbufen, Prosteglandin J2, Suxibuzone, Sulindac, and derivatives thereof.

Another embodiment provides a method for decreasing HSC growth by contacting a nascent stem cell population with at least one compound selected from the group consisting of Indomethacin, Fenbufen, NS398, SC560, Sulindac, Suxibuzone, Aspirin, Naproxen, Ibuprofen, Celecoxib, PGJ2, Aristolochic Acid, AH6809, AH23848, Kenpaullone, Valproic Acid, PD98059, KT5720, H89, U0126, Wortmannin, BayK 8644, Thiridazine, L-NAME, Enalapril, Captopril, AcSDKP, Losartan, AcSDKP, Losartan, Telimasartan, Histamine, Ambroxol, Chrysin, Cycloheximide, Methylene Blue, Epinephrine, Dexamethazone, Proadifen, Benzyl isothiocyanate, Ephedrine, Paragyline, Propranolol, Etanidazole, Methimazole, Cinoxacin, Penicillamine, Furosemide, Eburnamininone, Aclarubicin, Warfarin, Gamma-aminobutyric Acid, Norethindrone, Lupinidine, Hydroquinidine, Todralazine, Methoxamine, Hydroxyurea, Dihydroergotamine, Antazoline, 3-Nitropropionic Acid, N-Phenylanthranilic Acid, Phenazopyridine, Dichlorokynurenic acid, 3-estradiol, L-Leu, Phenoxybenzamine, Mephentermine, Guvacine, Guaiazulene, Imidazole, Beta-Carotene, Clofibrate, a PGE2 receptor antagonist, and derivatives of these compounds.

DESCRIPTION OF THE DRAWINGS

FIG. 2A shows microarray expression profiles of FACS sorted cell populations isolated during primitive (gata1 and lmo2) and definitive (lmo2 and cd41) hematopoiesis. Relative expression of cox1 (light gray) and cox-2 (dark gray) in each GFP+ sorted fraction compared to GFP− cells is shown. FIG. 2B shows the qPCR profiles of endothelial and HSC specific gene expression following exposure to long-acting dmPGE2 (10 µM, second bar in each triplet, dark gray) or the nonspecific cox inhibitor indomethacin (10 µM, third bar in triplet) versus control (first bar in triplet). Both treatments resulted in statistically significant differences compared to controls for each gene examined (ANOVA, $p<0.05$, $n=8$).

FIG. 4A shows representative FSC/SSC FACS profiles of hematopoietic cell lineages in the KM on days 0, 4, 7, 10 and 14 of irradiation recovery in DMSO and dmPGE2-treated (50 μM) zebrafish. FIG. 4B shows kinetics of KM reconstitution of precursor, lymphoid and myeloid cells in control fish (triangle) and dmPGE2-treated fish (square, 10 μM; circle, 50 μM).

FIG. 5A shows the effect of dmPGE2 treatment on stem cell and endothelial markers, as measured by qPCR on whole KM isolated on day three post-irradiation. An asterisk (*) indicates a statistically significant difference (two-tailed t-test, n=15, runx1: p=0.0001; lmo2: p=0.014; fli1: p=0.049). FIG. 5B depicts the effect of cox1 (SC560, 10 μM) and cox2 (NS398, 10 μM) inhibition on irradiation recovery (n=5/treatment). For fish treated with SC560 or NS398 no analysis could be obtained at day fourteen due to excessive death in these treatment groups.

FIG. 6A, Effect of increasing doses of dmPGE2 and inhibition of cyclooxygenase activity by indomethacin on hematopoietic differentiation in methylcellulose; numbers of definitive erythroid (E), mixed granulocyte/monocyte (GM), and multi-potent (GEMM) progenitor colonies are shown (10 μM dmPGE2: GM p=0.005, GEMM p=0.017; 20 μM dmPGE2: dE p=0.04, GM p=0.007, GEMM 0.016; 100 μM indomethacin: GM p=0.024). FIG. 6B, Effect of dmPGE2 and indomethacin on OP9 hematopoietic colony number (20 μM: p=0.047).

FIGS. 7A and 7B illustrate dmPGE2-mediated (10 μM) rescue of indomethacin (100 μM) inhibition of colony formation in (A) methylcellulose and (B) OP9 assays.

FIGS. 8A and 8B, Effect of ex vivo treatment of WBM (2 hrs on ice) with EtOH control or dmPGE2 (1 μM/106 cells) on CFU-S8 and CFU-S12 (60,000 cells/recipient; CFU-S12: two-tailed t-test, n=10, p<0.0001). FIG. 8C, Effect on CFU-S12 following ex vivo treatment with indomethacin (1 μM/106 cells) (100,000 cells/recipient; two-tailed t-test, n=10, p=0.0002). FIG. 8D, CFU-S12 evaluation after treatment of ckit+sca1+lineage-stem cells with dmPGE2 or EtOH control (two-tailed t-test, 100 cells: n=10, p=0.013; 300 cells: p=0.0003). FIGS. 8E and 8F, Limiting dilution competitive repopulation assay. The number of negative recipients as determined by FACS analysis (e) in relation to the total number of cells transplanted for control (square) or dmPGE2-treated (circle) cell samples is shown at 12 weeks. The frequency of engraftment (Panel F) at 6, 12, an 24 weeks post transplantation in recipients of EtOH versus dmPGE2-treated WBM calculated by Poisson statistics (ANOVA, n=10/variable, 6 wks: p=0.005; 12 wks: p=0.002; 24 wks: p=0.05); the number of recipients surviving to analysis at each time point is shown in Table 6-Table 8.

FIGS. 9A and 9B, Effect of ex vivo treatment of WBM and isolated HSCs with EtOH control or dmPGE2 on spleen weight on day (a) eight and (b) twelve (two-tailed t-test, CFU-$S_8$: n=5, p=0.339; CFU-$S_{12}$: n=9, p<0.00001). FIGS. 9M and 9N, Peripheral blood (day 14 post treatment) and bone marrow (day 16 post treatment) WBC counts following 5-FU bone marrow injury; in vivo exposure to SC560 or NS398 significantly inhibited WBC recovery, while dmPGE2 enhanced WBC counts.

FIG. 11A shows a schematic of the irradiation assay; FIG. 11B presents FACS analysis of whole kidney marrow on day ten post irradiation in wt, hs:wnt8, hs:dkk and hs:dnTCF adults.

DETAILED DESCRIPTION

Figure 1:
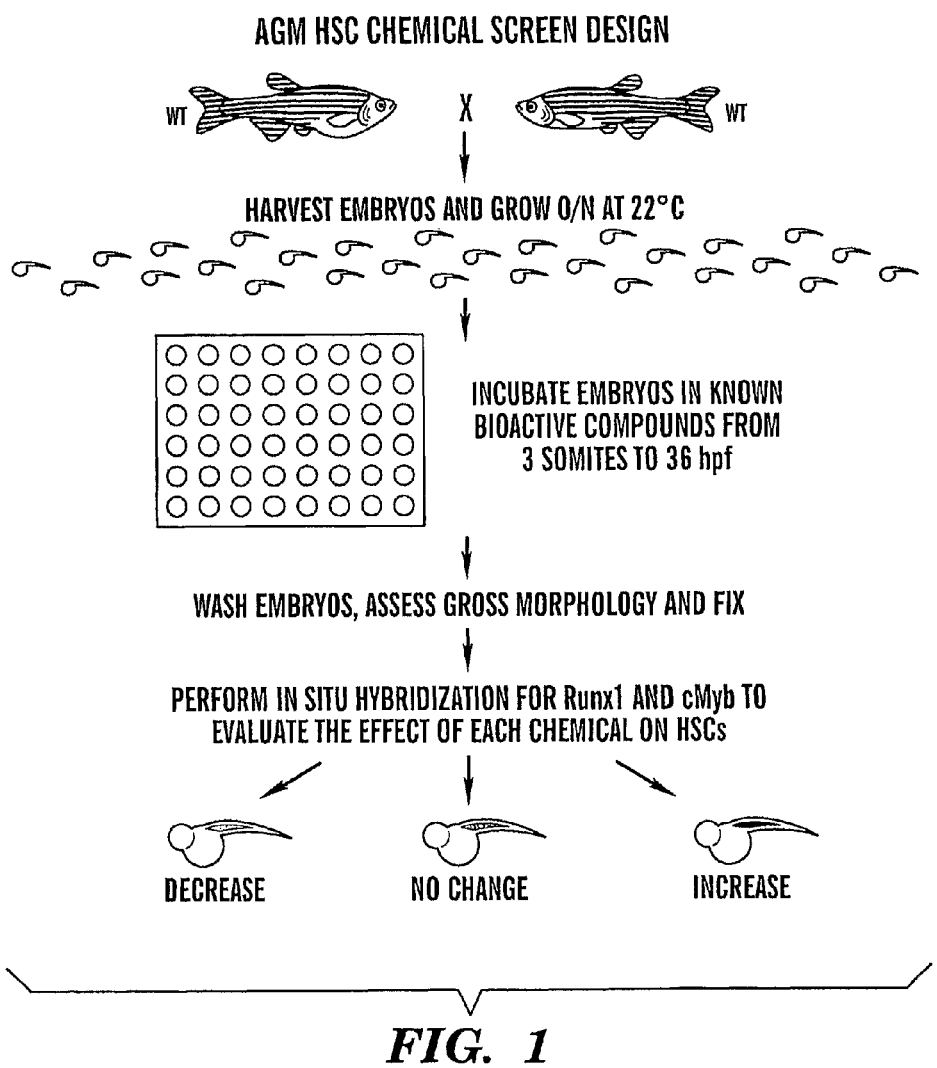
FIG. 1 presents a schematic of a screen for chemicals that affect stem cells in the AGM using Zebrafish embryos.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used in connection with percentages may mean±1%.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Hematopoietic stem cell (HSC) homeostasis it tightly controlled by growth factors, signaling molecules, and transcription factors. Definitive HCSs derived during embryogenesis in the aorta-gonad-mesonephros (AGM) region subsequently colonize the niche in fetal and adult hematopoietic organs. Dzierzak, 12 Curr. Opin. Hematol. 197-202 (2004); Galloway & Zon, 53 Curr. Top. Devel. Biol. 139-58 (2003).

The present invention provides methods for modulating HSC growth and renewal in vitro, in vivo, or ex vivo. The method comprises contacting a nascent stem cell population with at least one HSC modulator. This population may be contained within peripheral blood, cord blood, bone marrow, amniotic fluid, chorionic villa, placenta, or other hematopoietic stem cell niches. In one embodiment, the invention provides methods for promoting hematopoietic stem growth and renewal in a cell population. In another embodiment, the invention provides methods for inhibiting hematopoietic stem cell growth and renewal in a cell population.

The present invention is based, in part, on the discovery PGE2 and agents that enhance PGE2 synthesis cause an increase in HSC numbers. Conversely, agents that block PGE2 synthesis decrease HSCs. In that regard, agents affecting PGE2 synthesis may be considered HSC modulators. For example, the cyclooxygenases (cox) responsible for PGE2 synthesis may be required for HSC formation. Additionally, vasodilator agents promote HSC expansion, conversely, vasoconstrictors decrease HSC numbers. For example, hydralazine, an anti-hypertensive vasodialator, increased HSCs while fenbufen, a nonsteroidal anti-inflammatory drug vasoconstrictor decreased HSCs. These agents are thus also considered HSC modulators.

As used herein, HSC modulators may either promote or inhibit HSC growth and renewal. HSC modulators influence HSC numbers in a cell population. HSC modulators influence HSC expansion in culture (in vitro), during short term incubation, (ex vivo) or in vivo. See Table 1, below. HSC modulators that increase HSC numbers include agents that upregulate PGE2 synthesis. An increase in HSC numbers can be an increase of about 10%, about 20%, about 30%, about 40%, about 50%, about 60%, about 70%, about 80%, about 90%, about 100%, about 150%, about 200% or more, than the HSC numbers exhibited by the subject prior to treatment.

HSC modulators that cause a decrease in HSC numbers down-regulate PGE2 synthesis and/or promote vasoconstriction. See, for example, Table 2, below. A decrease in HSC numbers can be a decrease of about 10%, about 20%, about 30%, about 40%, about 50%, about 60%, about 70%, about 80%, about 90%, about 100%, about 150%, about 200% or more, than the HSC numbers exhibited by the subject prior to treatment. HSC numbers may be evaluated by the alleviation of the symptoms of the disease, for example, increased platelet count, increased hematocrit, wherein platelet count or hematocrit is increased about 10%, about 20%, about 30%, about 40%, about 50%, about 60%, about 70%, about 80%, about 90%, about 100%, about 150%, about 200% or more. The effect on HSC numbers may be evaluated by the alleviation of the symptoms of the disease, for example, increased platelet count, increased hematocrit, wherein platelet count or hematocrit is increased about 10%, about 20%, about 30%, about 40%, about 50%, about 60%, about 70%, about 80%, about 90%, about 100%, about 150%, about 200% or more.

In one embodiment, PGE2 or dmPGE2 are used as HSC modulators to increase the HSC population.

The HCS modulators of the present invention also include derivatives of HCS modulators. Derivatives, as used herein, include a chemically modified compound wherein the modification is considered routine by the ordinary skilled chemist, such as additional chemical moieties (e.g., an ester or an amide of an acid, protecting groups, such as a benzyl group for an alcohol or thiol, and tert-butoxycarbonyl group for an amine). Derivatives also include radioactively labeled HSC modulators, conjugates of HSC modulators (e.g., biotin or avidin, with enzymes such as horseradish peroxidase and the like, with bioluminescent agents, chemoluminescent agents or fluorescent agents). Additionally, moieties may be added to the HCS modulator or a portion thereof to increase half-life in vivo. Derivatives, as used herein, also encompasses analogs, such as a compound that comprises a chemically modified form of a specific compound or class thereof, and that maintains the pharmaceutical and/or pharmacological activities characteristic of said compound or class, are also encompassed in the present invention. Derivatives, as used herein, also encompasses prodrugs of the HCS modulators, which are known to enhance numerous desirable qualities of pharmaceuticals (e.g., solubility, bioavailability, manufacturing, etc.).

Direct ex vivo administration of HSC modulators can enable significant in vivo expansion of hematopoietic stem cells, such that even smaller amounts of hematopoietic stem cells can then be enough in transplantation. Consequently, for example, cord blood stem cell transplantation may now be applied to not only children but also adults. Such stem cells may be collected from sources including, for example, peripheral blood, cord blood, bone marrow, amniotic fluid, or placental blood. Alternatively, the HSC-containing source sample may be harvested and then stored immediately in the presence of a HSC modulator, such as PGE2, and initially incubated (prior to differentiation) in the presence of the HSC modulator before introduction into a subject.

Additionally, one or more HSC modulators can be used in vivo to increase the number of stem cells in bone marrow or other sources (such as cord blood). By increasing the number of stem cells, the total harvest of stem cells from the subject can be significantly improved. Further, by increasing the number of stem cells harvested from the subject, the number of stem cells available for transplantation back into the subject or to another subject can also be significantly improved, thereby potentially reducing the time to engraftment, and consequently leading to a decrease in the time during which the subject has insufficient neutrophils and platelets, thus preventing infections, bleeding, or other complications.

In addition, the present invention can reduce the proportion of subjects who are otherwise unable to mobilize enough cells for stem cell harvest to proceed with treatment for their primary illness, e.g., chemotherapy and other bone marrow ablative treatments. Thus, the proportion of the number of subjects with delayed primary engraftment can also be reduced. Furthermore, the present invention can promote recovery subsequent to bone marrow ablative treatments by increasing HSC numbers.

HSC modulators, such as those in Table 1 and disclosed herein, can be used in vivo to increase HSC production and ex vivo to increase HSC number. This is accomplished by administering one or more of the compounds to a subject or to the stem cells.

HSC modulators can also be used to provide autologous HSCs to a subject. Typically, this involves the steps of administering HSC modulators to a subject in need thereof to enhance expansion of the stem cell population within bone marrow and/or to mobilize the stem cells in peripheral circulation; harvesting one or more of the bone marrow stem cells or one or more of the stem cells in the peripheral circulation; and transplanting the one or more harvested stem cells back into the subject.

In addition, the stem cells obtained from harvesting according to method of the present invention described above can be cryopreserved using techniques known in the art for stem cell cryopreservation. Accordingly, using cryopreservation, the stem cells can be maintained such that once it is determined that a subject is in need of stem cell transplantation, the stem cells can be thawed and transplanted back into the subject As noted previously, the use of one or more HSC modulators, for example PGE2, during cryopreservation techniques may enhance the HSC population.

More specifically, another embodiment of the present invention provides for the enhancement of HSCs collected from cord blood or an equivalent neonatal or fetal stem cell source, which may be cryopreserved, for the therapeutic uses of such stem cells upon thawing. Such blood may be collected by several methods known in the art. For example, because umbilical cord blood is a rich source of HSCs (see Nakahata & Ogawa, 70 J. Clin. Invest. 1324-28 (1982); Prindull et al., 67 Acta. Paediatr. Scand. 413-16 (1978); Tchernia et al., 97(3) J. Lab. Clin. Med. 322-31 (1981)), an excellent source for neonatal blood is the umbilical cord and placenta. The neonatal blood may be obtained by direct drainage from the cord and/or by needle aspiration from the delivered placenta at the root and at distended veins. See, e.g., U.S. Pat. No. 7,160,714; No. 5,114,672; No. 5,004,681; U.S. patent application Ser. No. 10/076,180, Pub. No. 20030032179.

Indeed, umbilical cord blood stem cells have been used to reconstitute hematopoiesis in children with malignant and nonmalignant diseases after treatment with myeloablative doses of chemo-radiotherapy. Sirchia & Rebulla, 84 Haematologica 738-47 (1999). See also Laughlin 27 Bone Marrow Transplant. 1-6 (2001); U.S. Pat. No. 6,852,534. Additionally, it has been reported that stem and progenitor cells in cord blood appear to have a greater proliferative capacity in culture than those in adult bone marrow. Salahuddin et al., 58 Blood 931-38 (1981); Cappellini et al., 57 Brit. J. Haematol. 61-70 (1984).

Alternatively, fetal blood can be taken from the fetal circulation at the placental root with the use of a needle guided by ultrasound (Daffos et al., 153 Am. J. Obstet. Gynecol. 655-60 (1985); Daffos et al., 146 Am. J. Obstet. Gynecol. 985-87 (1983), by placentocentesis (Valenti, 115 Am. J. Obstet. Gynecol. 851-53 (1973); Cao et al., 19 J. Med. Genet. 81-87 (1982)), by fetoscopy (Rodeck, in PRENATAL DIAGNOSIS, (Rodeck & Nicolaides, eds., Royal College of Obstetricians & Gynaecologists, London, 1984)). Indeed, the chorionic villus and amniotic fluid, in addition to cord blood and placenta, are sources of pluripotent fetal stem cells (see WO 2003 042405) that may be treated by the HCS modulators of the present invention.

Various kits and collection devices are known for the collection, processing, and storage of cord blood. See, e.g., U.S. Pat. No. 7,147,626; No. 7,131,958. Collections should be made under sterile conditions, and the blood may be treated with an anticoagulant. Such an anticoagulants include citrate-phosphate-dextrose, acid citrate-dextrose, Alsever's solution (Alsever & Ainslie, 41 N.Y. St. J. Med. 126-35 (1941), DeGowin's Solution (DeGowin et al., 114 J.A.M.A. 850-55 (1940)), Edglugate-Mg (Smith et al., 38 J. Thorac. Cardiovasc. Surg. 573-85 (1959)), Rous-Turner Solution (Rous & Turner 23 J. Exp. Med. 219-37 (1916)), other glucose mixtures, heparin, or ethyl biscoumacetate. See Hurn Storage of Blood 26-160 (Acad. Press, NY, 1968).

Various procedures are known in the art and can be used to enrich collected cord blood for HCSs. These include but are not limited to equilibrium density centrifugation, velocity sedimentation at unit gravity, immune resetting and immune adherence, counterflow centrifugal elutriation, T lymphocyte depletion, and fluorescence-activated cell sorting, alone or in combination. See, e.g., U.S. Pat. No. 5,004,681.

Typically, collected blood is prepared for cryogenic storage by addition of cryoprotective agents such as DMSO (Lovelock & Bishop, 183 Nature 1394-95 (1959); Ashwood-Smith 190 Nature 1204-05 (1961)), glycerol, polyvinylpyrrolidine (Rinfret 85 Ann. N.Y. Acad. Sci. 576-94 (1960)), polyethylene glycol (Sloviter & Ravdin 196 Nature 899-900 (1962)), albumin, dextran, sucrose, ethylene glycol, i-erythritol, D-ribitol, D-mannitol (Rowe, 3(1) Cryobiology 12-18 (1966)), D-sorbitol, i-inositol, D-lactose, choline chloride (Bender et al., 15 J. Appl. Physiol. 520-24 (1960)), amino acids (Phan & Bender, 20 Exp. Cell Res. 651-54 (1960)), methanol, acetamide, glycerol monoacetate (Lovelock, 56 Biochem. J. 265-70 (1954)), and inorganic salts (Phan & Bender, 104 Proc. Soc. Exp. Biol. Med. (1960)). Addition of plasma (e.g., to a concentration of 20-25%) may augment the protective effect of DMSO.

Collected blood should be cooled at a controlled rate for cryogenic storage. Different cryoprotective agents and different cell types have different optimal cooling rates. See e.g., Rapatz, 5(1) Cryobiology 18-25 (1968), Rowe & Rinfret, 20 Blood 636-37 (1962); Rowe, 3(1) Cryobiology 12-18 (1966); Lewis et al., 7(1) Transfusion 17-32 (1967); Mazur 168 Science 939-49 (1970). Considerations and procedures for the manipulation, cryopreservation, and long-term storage of HSC sources are known in the art. See e.g., U.S. Pat. No. 4,199,022; U.S. Pat. No. 3,753,357; U.S. Pat. No. 4,559,298; U.S. Pat. No. 5,004,681. There are also various devices with associated protocols for the storage of blood. U.S. Pat. No. 6,226,997; U.S. Pat. No. 7,179,643

Considerations in the thawing and reconstitution of HCS sources are also known in the art. U.S. Pat. No. 7,179,643; U.S. Pat. No. 5,004,681. The HCS source blood may also be treated to prevent clumping (see Spitzer, 45 Cancer 3075-85 (1980); Stiff et al., 20 Cryobiology 17-24 (1983), and to remove toxic cryoprotective agents (U.S. Pat. No. 5,004,681). Further, there are various approaches to determining an engrafting cell dose of HSC transplant units. See U.S. Pat. No. 6,852,534; Kuchler Biochem. METHODS IN CELL CULTURE & VIROLOGY 18-19 (Dowden, Hutchinson & Ross, Strodsburg, Pa., 1964); 10 Methods in Medical Research 39-47 (Eisen, et al., eds., Year Book Med. Pub., Inc., Chicago, Ill., 1964).

Thus, not being limited to any particular collection, treatment, or storage protocols, an embodiment of the present invention provides for the addition of an HSC modulator, such as PGE2 or dmPGE2 to the neonatal blood. This may be done at collection time, or at the time of preparation for storage, or upon thawing and before infusion.

For example, stem cells isolated from a subject, e.g., with or without prior treatment of the subject with HSC modulators, may be incubated in the presence of HSC modulators, e.g., HSC modulators such as PGE2 or those listed in Table 1, in order to expand the number of HSCs. Expanded HSCs may be subsequently reintroduced into the subject from which they were obtained or may be introduced into another subject.

The HSC modulators, including PGE2 and the compounds set forth in Table 1 and disclosed herein, can thus be used for, inter alia: reducing the time to engraftment following reinfusion of stem cells in a subject; reducing the incidence of delayed primary engraftment; reducing the incidence of secondary failure of platelet production; and reducing the time of platelet and/or neutrophil recovery following reinfusion of stem cells in a subject. These methods typically include the steps of administering an HSC modulator to a subject in need thereof to enhance expansion of the stem cell population within bone marrow and/or mobilize the stem cells in peripheral circulation and then harvesting one or more of the bone marrow stem cells or the stem cells in the peripheral circulation and then transplanting the harvested stem cell back into the subject at the appropriate time, as determined by the particular needs of the subject.

The HSC modulators, e.g., HSC modulators that cause an increase HSC numbers, can provide a convenient single dose therapy to improve the efficiency of stem cell transplantation, to permit more aggressive treatment of solid tumors, myeloma and lymphoma and to increase the number of candidates for stem cell transplantation.

The method of the invention may also be used to increase the number of stem cells from a donor subject (including bone marrow cells or cord blood cells), whose cells are then used for rescue of a recipient subject who has received bone marrow ablating chemotherapy or irradiation therapy.

As used herein, a subject includes anyone who is a candidate for autologous stem cell or bone marrow transplantation during the course of treatment for malignant disease or as a component of gene therapy. Other possible candidates are subjects who donate stem cells or bone marrow to subjects for allogeneic transplantation for malignant disease or gene therapy. Subjects may have undergone irradiation therapy, for example, as a treatment for malignancy of cell type other than hematopoietic. Subjects may be suffering from anemia, e.g., sickle cell anemia, thalessemia, aplastic anemia, or other deficiency of HSC derivatives.

The method of the invention thus provides the following benefits: (1) Allows transplantation to proceed in patients who would not otherwise be considered as candidates because of the unacceptably high risk of failed engraftment; (2) Reduces the number of aphereses required to generate a minimum acceptable harvest; (3) Reduces the incidence of primary and secondary failure of engraftment by increasing the number HSCs available for transplantation; and (4) Reduces the time required for primary engraftment by increasing the number of committed precursors of the important hemopoietic lineages.

The HSC modulators of the invention may have the clinical benefits in stem cell transplantation of improvement of apheresis yields and improvement of the engraftment potential of apheresed cells.

The HSC modulators of the invention, e.g., HSC modulators that cause a decrease of HSC numbers, may also be of use in treating subjects suffering from hyperproliferative disorders of the hematopoietic system. Hyperproliferative disorders may include, but are not limited to, polycythemia vera, essential thrombocythemia, myelofibrosis with myeloid metaplasia, and chronic myelogenous leukemia.

The compounds or agents of the present invention can be contained in pharmaceutically acceptable formulations. Such a pharmaceutically acceptable formulation may include a pharmaceutically acceptable carrier(s) and/or excipient(s). As used herein, "pharmaceutically acceptable carrier" includes any and all solvents, dispersion media, coatings, antibacterial and anti fungal agents, isotonic and absorption delaying agents, and the like that are physiologically compatible. For example, the carrier can be suitable for injection into the cerebrospinal fluid. Excipients include pharmaceutically acceptable stabilizers. The present invention pertains to any pharmaceutically acceptable formulations, including synthetic or natural polymers in the form of macromolecular complexes, nanocapsules, microspheres, or beads, and lipid-based formulations including oil-in-water emulsions, micelles, mixed micelles, synthetic membrane vesicles, and resealed erythrocytes.

When the agents or compounds are delivered to a patient, they can be administered by any suitable route, including, for example, orally (e.g., in capsules, suspensions or tablets) or by parenteral administration. Parenteral administration can include, for example, intramuscular, intravenous, intraarticular, intraarterial, intrathecal, subcutaneous, or intraperitoneal administration. The agent can also be administered orally, transdermally, topically, by inhalation (e.g., intrabronchial, intranasal, oral inhalation or intranasal drops) or rectally. Administration can be local or systemic as indicated. Agents can also be delivered using viral vectors, which are well known to those skilled in the art.

Both local and systemic administration are contemplated by the invention. Desirable features of local administration include achieving effective local concentrations of the active compound as well as avoiding adverse side effects from systemic administration of the active compound. In a preferred embodiment, the antagonist is administered locally. Localized delivery techniques are described in, for example, 51 J. Biomed. Mat. Res. 96-106 (2000); 100(2) J. Control Release 211-19 (2004); 103(3) J. Control Release 541-63 (2005); 15(3) Vet. Clin. North Arm. Equine Pract. 603-22 (1999); 1(1) Semin. Interv. Cardiol. 17-23 (1996)

The pharmaceutically acceptable formulations can be suspended in aqueous vehicles and introduced through conventional hypodermic needles or using infusion pumps.

The amount of agent administered to the individual will depend on the characteristics of the individual, such as general health, age, sex, body weight and tolerance to drugs as well as the degree, severity and type of rejection. The skilled artisan will be able to determine appropriate dosages depending on these and other factors.

HSC modulators within the scope of the present invention may be identified in a variety of ways, such as the zebrafish genetic system. The zebrafish is an excellent genetic system for the study of vertebrate development and diseases. See e.g., Hsia & Zon, 33(9) Exp. Hematol. 1007-14 (2005); de Jong & Zon; 39 Ann. Rev. Genet. 481-501 (2005); Paffett-Lugassy & Zon, 105 Meth. Mol. Med. 171-98 (2005); Haffner & Nusslein-Volhard, 40 Int'l J. Devel. Biol. 221-27 (1996). The embryo developing externally is transparent and organs can be easily visualized. Zebrafish and mammals share many of the same gene programs in development. When zebrafish mate, they give rise to large numbers (100-200 weekly) of transparent embryos. Many embryos can be placed in a relatively small space, and there is a short generation time (about 3 months). Large-scale screens have generated more than 2000 genetic mutants with specific defects that affect virtually every aspect of embryogenesis. Driever et al., 123 Devel. 37-46 (1996); Eisen, 87 Cell 969-77 (1996). Many of the blood mutants have been useful in describing key events in hematopoeisis. Dooley & Zon, 10 Curr. Op. Genet. Devel. 252-56 (2000). Zebrafish have been used to perform whole organism-based small molecule screens because large numbers of the embryos can be arrayed into microtiter plates containing compounds from a chemical library. For example, Peterson and colleagues tested 1,100 compounds for developmental defects. Peterson et al., 97 P.N.A.S. USA 12965-69 (2000). From this screen, about 2% of the compounds were lethal, and 1% caused a specific phenotype. For example, one compound suppressed formation of inner ear structures called otoliths, but caused no other defects.

It is also possible to screen for chemical suppressors of mutant phenotypes. Peterson et al., 22 Nat. Biotech. 595-99 (2004); Stern et al., 1 Nat. Chem. Biol. 0.366-70 (2005). In one such screen, chemicals were found to rescue the gridlock mutant, a model of congenital coarctation of the aorta. Peterson et al., 2004. The mechanism of this rescue involved the induction of VEGF which corrected the angiogenesis defect. These data demonstrate that highly potent and specific compounds can be identified using zebrafish.

Further regarding zebrafish, a high-density genetic map has been constructed that includes microsatellite markers, genes, and expressed sequence tags (ESTs). Knapuk et al., 18 Nat. Genet. 338-43 (1998); Shimoda et al., 58 Genomic 219-32 (1999); Kelly et al., 10 Genome Res. 558-67 (2000); Woods et al., 20 Genome Res. 1903-14 (2000). A full-length cDNA project has also been undertaken as an extension to the zebrafish EST project. A dense RH map has been constructed and integrated with data for the genome sequencing project at the Sanger Center. An important web resource supported by the NIH is the zebrafish information network (ZFIN), a focal point for the community. A stock center and supportive laboratory called the Zebrafish International Resource Center (ZIRC) also greatly helps the field. The Sanger Center is sequencing the zebrafish genome which may be completed in 2007.

The onset of definitive hematopoiesis has been studied in a number of vertebrate species. In seminal work in the avian species, chick-quail chimeras demonstrated that definitive hematopoietic stem cells do not arise on the yolk sac, but arise within the embryo proper. Dieterien-Lievre 33 J. Embryol. Exp. Morphol. 607-19 (1975). Similar studies in the *Xenopus* embryo using diploid/triploid chimeras elucidated that the ventral blood island (the yolk sac equivalent) played a minor role in adult hematopoiesis compared to the dorsal lateral plate. Kau & Turpen 131 J. Immunol. 2262-66 (1983). Based on the finding that the dorsolateral plate mesoderm contained putative hematopoietic cells that gave rise to definitive hematopoiesis, several groups further investigated the developing aorta gonad mesonephros (AGM) region. Medvinsky et al., 364 Nature 64-67 (1993); Godin et al., 364 Nature 67-70 (1993). Within this region, there are clusters of cells in the ventral wall of the aorta that were originally recognized in the pig. Sabin, 9 Contrib. to Embryol. 213-62 (1920). Others have suggested that these clusters represent early hematopoietic stem cells that are derived from "hemogenic" endothelial cells.

The process of AGM hematopoiesis is evolutionarily conserved in the vertebrate. Galloway & Zon, 53 Curr. Topics Dev. Biol. 139-58 (2003). In mouse, the onset of stem cells occurs at 8.5 days to 9 days, just as circulation is beginning. Hematopoietic stem cells of the AGM region at day eleven can be transplanted, however, the cells at day ten will not lead to long term engraftment. Further studies have elucidated that the aorta is polarized, and factors from the ventral and dorsal regions will modify the behavior of cells. For instance, the dorsal region of the aorta is derived from somitic mesoderm. It is under the influence of TGFα, BMP, and sonic hedgehog signaling. Parnanud & Dieterlen-Lievre, 126 Devel. 617-27 (1999).

Cell marking studies have demonstrated that the putative HSC in the AGM have the potential to invade the subaortic mesenchyme and also a variety of tissues. Jaffredo et al., 125 Devel. 4575-83 (1998); Jaffredo et al., 224 Devel. Biol. 204-14 (2000). These cell marking studies used India ink or cells infected by retroviruses tagged with LacZ infused into the vasculature. These fate mapping experiments showed labeling of hematopoietic cells within tissues. These studies elucidate the onset of hematopoietic stem cells within the aorta in the vertebrate embryo Several genes have been found to be required for AGM hematopoiesis. The gene, runx1 (previously AML1 oncoprotein), is expressed in the aortic wall in the ventral region where the hematopoietic cells are found; this gene function is required for AGM hematopoiesis. Cal et al., 13 Immunity 423-31 (2000). The runx1 mutant mouse lacks an AGM and has defective hematopoiesis. The defect in the runx1 mutant can be rescued by a runx1 transgene driven by the Tie2 promoter, demonstrating that endothelial and hematopoietic driven expression of runx1 is sufficient to regulate AGM hematopoiesis. Miller et al., 32 Nature Genet. 645-49 (2002). In a runx1 knock-in, there are subaortic mesenchymal cells that are labeled with LacZ, and this observation has been interpreted to mean that some of the subaortic cells may give rise to hematopoietic stem cells. North et al., 126 Devel. 2563-75 (1999). Recent studies, have demonstrated that the subaortic endothelial cells push through the endothelial layer and form hematopoietic clusters. Bertrand et al., 102 P.N.A.S. USA 134-39 (2005); Tavian & Peault, 33 Exp. Hemat. 1062-69 (2005); Tavian & Peault, 49 Int'l J. Devel. Biol. 243-50 (2005); Tavian et al., 1044 Ann. NY Acad. Sci. 41-50 (2005).

Thus, it may be disputed whether the hemogenic endothelial cells or the subaortic mesodermal cells are the true precursors of HSCs. Once the hematopoietic stem cells bud off the endothelial wall, they are CD45+ and express the transcription factors runx1 and c-myb. The AGM cells are also under control by notch signaling. The notch1 knock-out mouse AGM hematopoietic stem cells and runx1 and c-myb expression are absent in the aorta region. Kumano et al., 18 Immunity 699-711 (2003); Robert-Moreno et al., 132 Devel. 1117-26 (2005). In addition, the coupTF transcription factor also lacks AGM hematopoietic stem cells, although it has not been studied as thoroughly. You et al., 435 Nature 98-104 (2005). Although runx1, cymb, notch, and coup appear to be important for AGM hematopoiesis, the interaction, temporal and spatial relation of these factors, and role of other potentially unknown factors is not known. A better understanding of the genetic program of the onset of hematopoiesis is clearly necessary.

A chemical genetic screen was conducted to identify novel pathways that modulate definitive HSC formation during zebrafish embryogenesis. FIG. 1. Genes such as runx1 and cmyb, required for HSC development during mammalian hematopoiesis, are expressed in the ventral wall of the dorsal aorta in a region analogous to the mammalian AGM at thirty-six hours post-fertilization (hpf). North et al., 16 Immunity 661-72 (2002); Mukouyama et al., 9 Curr. Biol. 833-86 (1999); Kalev-Zylinska et al., 129 Devel. 2015-30 (2002); Burns et al., 30 Exp. Hematol. 1381-89 (2002). Wild-type embryos were incubated with individual compounds from the three-somite stage until thirty-six hpf. Probes for runx1 and cmyb were combined and utilized to detect HSCs by in situ hybridization. The majority of chemicals, 2275 of 2357 (91.7%), failed to alter runx1/cmyb expression, while 35 (1.4%) and 47 (1.9%) led to increased or decreased AGM HSCs, respectively.

Of the eighty-two substances that changed runx1/cmyb expression, ten affect the prostaglandin (PG) pathway. PGs are formed from arachidonic acid by cox1, cox2, and tissue specific isomerases. At least five PG pathway compounds increased HSC gene expression (Table 1), and five decreased HSC gene expression (Table 2). At thirty-six hpf, runx1/cmyb+HSCs comprise a line of flattened endothelial cells and hematopoietic clusters in the aorta. Linoleic acid (10 µM), a PG precursor, increased runx1/cmyb+HSCs (22 altered/30 scored) whereas celecoxib (20 µM), a selective inhibitor of cox2, decreased HSCs (26/31). The vascular marker flk1 remained relatively unchanged. Prostaglandin E2 is the main effector prostanoid produced in the zebrafish (Grosser et al., 99 P.N.A.S. USA 8418-23 (2002)), and is regulated by both cox1 and cox2. Zebrafish embryos were exposed to inhibitors of prostaglandin synthesis, as well as exogenous prostanoids. Treatment with PGE2 (25/49) resulted in stronger expression of runx1/cmyb than PGI2 (28/47) at 20 µM, while the isoform-selective inhibition of cox activity with SC560 (cox1, 10 µM, 30/36) and NS398 (cox2, 20 µM, 35/44) as well as non-specific cox inhibitors led to decreased HSCs. These findings argue persuasively for a specific role of PGs in the formation of AGM HSCs.

TABLE 1

Example HSC modulators that increase HSCs

| Compound | # Times Identified | Effect on HSC expression (# embryos altered/ # embryos scored) |
|---|---|---|
| Mead Acid | 2 | Increase (24/32) |
| Linoleic Acid | 1 | Increase (22/30) |
| 13(S)-HODE | 1 | Increase (15/25) |
| Ly-171883 | 1 | Increase (17/26) |
| Epoxyeicosatrienoic Acid | 1 | Increase (17/25) |

PG pathway compounds identified as modulating runx1/cmyb[+] HSCs are listed in column one. Column two denotes the frequency at which a particular compound was identified. The third column shows the effect of the compound on HSC gene expression (# embryos altered/# embryos scored).

TABLE 2

Example HSC modulators that decrease HSCs

| Compound | # Times Identified | Effect on HSC expression (# embryos altered/ # embryos scored) |
|---|---|---|
| Celecoxib | 2 | Decrease (26/31) |
| Fenbufen | 1 | Decrease (20/26) |
| Prosteglandin J2 | 1 | Decrease (12/22) |
| Suxibuzone | 1 | Decrease (16/30) |
| Sulindac | 1 | Decrease (18/31) |

PG pathway compounds identified as modulating runx1/cmyb[+] HSCs are listed in column one. Column two denotes the frequency at which a particular compound was identified. The third column shows the effect of the compound on HSC gene expression (# embryos altered/# embryos scored).

Additional HSC prostaglandin pathway modifiers were identified using the zebrafish screening techniques described herein such as those shown in Table 3:

TABLE 3

Example prostaglandin pathway modifiers

| HSC Inhibitors | HSC Enhancers |
|---|---|
| Indomethacin | dmPGE2 |
| SC560 | PGE2 |
| NS398 | PGI2 |
| Aspirin | Eicosatrienoic Acid |
| Ibuprofen | ONO-259 |
| Naproxen | Cay10397 |
| Aristolochic Acid | |
| AH6809 (EP½ antag) | |
| AH23848 (EP4 antag) | |

Figure 2A:
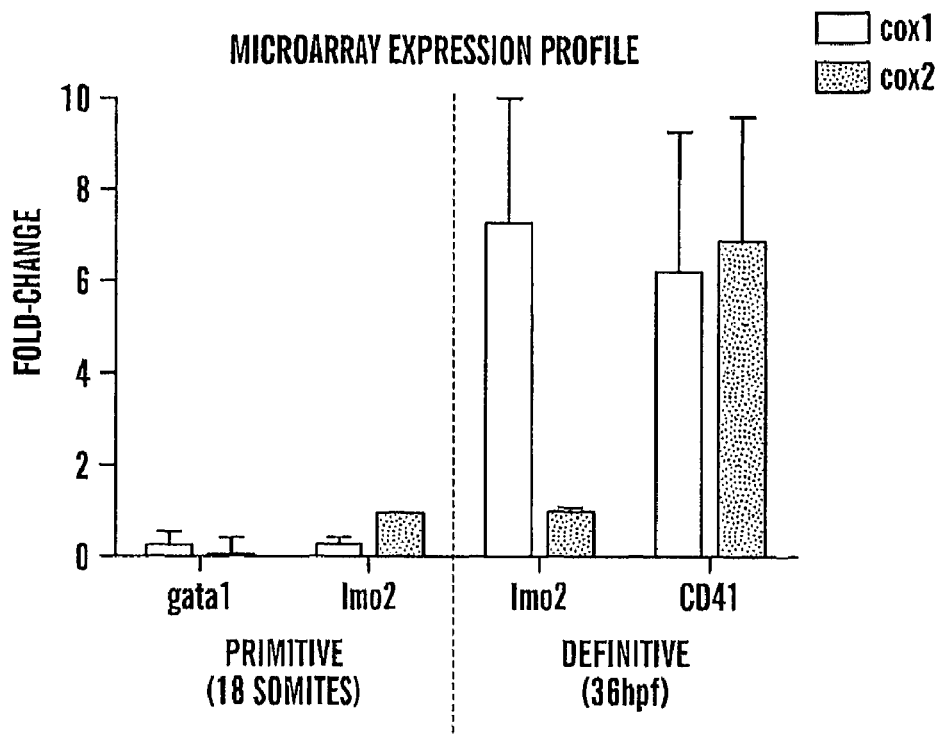
FIGS. 2A and 2B relate to prostaglandin agonists and antagonists that alter runx1/cmyb expression without affecting vascular development.
Figure 2B:
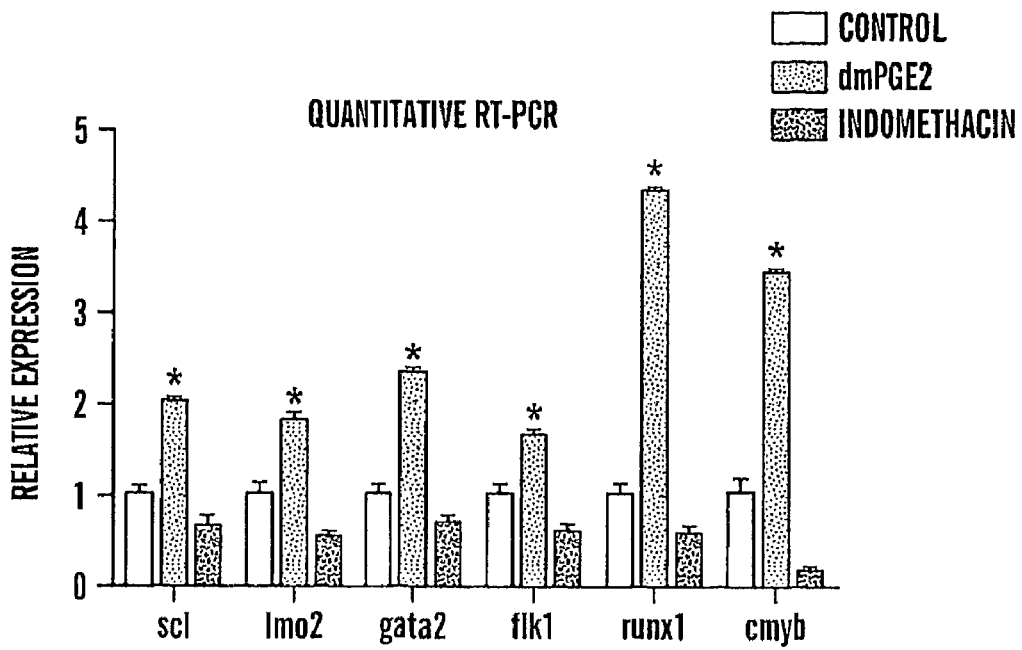

The expression of cox1 in the vasculature was described previously; knock-down of cox1 activity inhibited the development of the endothelial boundary between the aorta and vein. Cha et al., 282 Devel. Biol. 274-83 (2005). As HSCs arise from a hemogenic endothelial cell population, loss of cox1 function would impact HSC development. By in situ hybridization, cox2 was diffusely expressed in the tail region encompassing the AGM at thirty-six hpf. In FACS-isolated blood and endothelial cell populations, both cox1 and cox2 were found to be upregulated during the switch from primitive to definitive hematopoiesis. High levels of cox1 expression were detected in both lmo2+ endothelial cells and in CD41+HSCs, while cox2 was only upregulated in the HSC fraction (FIG. 2, Panel A). These results suggest that cox1 and cox2 participate in the induction of AGM HSCs through regulation of stem cell niche, as well as in the HSC itself.

Linoelic Acid and Mead Acid can act as substrates for prostaglandin production and were isolated in the screen as agents that upregulated HSC formation. To determine which prostaglandin was mediating the increase in HSCs in the AGM, zebrafish were exposed to exogenous purified prostaglandins from three somites to 36 hpf and stained as described previously. In the zebrafish, the major physiologically active prostaglandins are PGE2, PGI2 and PGF2. Pini et al., 25 Arterioscler. Thromb. Vasc. Biol. 315-20 (2005); Grosser et al., 2002. Each of these was tested for their effect on AGM HSCs. Both PGE2 and PGI2, were found to increase moderately the numbers of Runx1+Cmyb+ cells in the AGM, while PGF2 had no effect. Due to the tight regulation of prostaglandin production and destruction in vivo, a slowly metabolized version of PGE2 was also examined.

Figure 3:
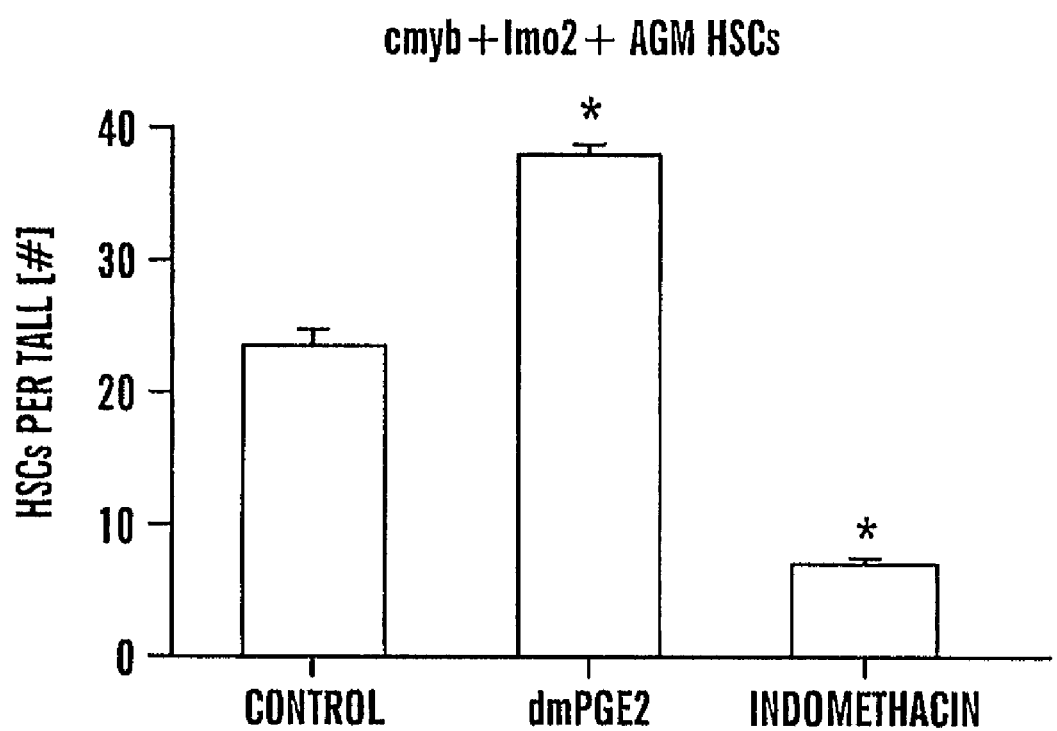
FIG. 3 depicts data indicating that prostaglandin agonists and antagonists alter runx1/cmyb expression by quantitative analysis of HSC numbers in bigenic zebrafish embryos detected by confocal microscopy: DMSO 23.3±5.0 (mean±SD), dmPGE2 (10 μM) 38.0±2.2, indomethacin (10 μM) (ANOVA, p<0.00001, n=10/treatment).

A long-acting derivative, 16,16-dimethyl-PGE2 (dmPGE2, 10 µM) caused an increase in runx1/cmyb+AGM HSCs in 78% of embryos examined (97/124). AGM HSCs were inhibited by indomethacin (10 µM) treatment in 90% of embryos analyzed (92/102). PGE2 was the most abundant PG measured by mass spectrometry in 36 hpf embryos (18+/−6 pg/50 embryos; n=4), and indomethacin treatment depressed PGE2 formation below detectable levels (<2 pg/50 embryos; n=−3)7. Treatment with dmPGE2 had minimal effects on the vasculature by flk1 staining; indomethacin slightly altered the intersomitic vessels in 30% of embryos examined (15/49). Transgenic cmyb:GFP zebrafish with green fluorescent HSCs and myeloid progenitor cells were crossed to lmo2:dsRed fish that have red fluorescent endothelial cells and HSCs to visualize the effects of chemical exposure in vivo. At 36 hpf, live embryos imaged by confocal microscopy exhibited significantly decreased numbers of HSCs along the floor of the aorta following indomethacin treatment, and significantly increased HSCs after dmPGE2 exposure. FIG. 3. This indicates that PG affects the total number of HSCs formed along the dorsal wall of the aorta; induction of HSCs at aberrant locations is not evident. By qPCR runx1 expression was 3-fold enhanced after addition of dmPGE2, while indomethacin caused a significant 50% reduction in runx1 expression; significant alterations in the expression of cmyb were also observed (FIG. 2, Panel B).

To confirm the requirement of PGE2 activity, low-dose (40 μM) morpholino oligonucleotides (MO) was used to knock down expression of cox1 and cox2; low dose inhibition of cox1 activity allowed embryos to proceed through gastrulation, while mimicking cox-dependent developmental defects. Grosser et al., (2002). MO inhibition of cox decreased AGM HSCs (cox1 54/74; cox2 60/71). Mass spectroscopy analysis demonstrated PGE2 was below detectable levels in these embryos, consistent with MO-mediated suppression of endogenous prostaglandin synthesis (n=4). The effects on HSCs were reversed by incubation of MO-injected embryos with 10 μM dmPGE2 (cox1/dmPGE2 29/52 rescued; cox2/dmPGE2 43/60). MO knockdown of PGE2 synthase caused a reduction of HSCs (35/50), which was rescued by dmPGE2 addition (25/45), indicating that signaling through PGE2 was sufficient to modulate HSC formation. PGE2 signals through several receptors, EP 1-4, all of which are present in the zebrafish genome. Cha et al., 20 Genet. Devel. 77-86 (2002). MO knockdown of the EP2 and EP4 receptors resulted in diminished runx1/cmyb expression (EP2 39/63; EP4 44/67) that was not reversed by exposure to exogenous dmPGE2. Analysis by qPCR demonstrated that EP2 and EP4 were present in both CD41+HSC and CD41− non-stem cell FACS sorted cell populations at 36 hpf. These experiments confirm that PGE2-mediated signaling regulates the formation of HSCs in the AGM region.

To further explore the interactions between prostaglandins and HSC production, numerous prostaglandin derivatives were screened using the zebrafish embryo technique described herein. In general, the assays indicated that derivatives that enhanced stability of PGE2 increased HSCs. Those for which no enhancement was observed relative to controls tended to be compounds that bound preferentially to the receptors that were not active in HSCs. The effects of these compounds on HSC numbers are indicated in Table 4:

TABLE 4

Prostaglandin derivatives effecting HSC production

| | |
|---|---|
| ⇧ | PGE2 |
| ⇧⇧ | 16,16-dimethyl PGE2 |
| | 20-hydroxy PGE2 |
| ⇧⇧ | 19(R)-hydroxy PGE2 |
| ⇧⇧ | 16,16-dimethyl PGE2 p-(p-acetamidobenzamido) phenyl ester |
| ⇧ | 11-deoxy-16,16-dimethyl PGE2 |
| ⇧⇧ | 9-deoxy-9-methylene-16,16-dimethyl PGE2 |
| ⇧⇧ | 9-deoxy-9-methylene PGE2 |
| | 9-keto Fluprostenol |
| ⇧ | Butaprost |
| ⇧ | Sulprostone |
| toxic | 5-trans PGE2 |
| | 17-phenyl trinor PGE2 |
| ⇧ | PGE2 serinol amide |
| ⇧⇧ | PGE2 methyl ester |
| ⇧⇧⇧ | 16-phenyl tetranor PGE2 |
| ⇧⇧ | 15(S)-15-methyl PGE2 |
| ⇧⇧ | 15(R)-15-methyl PGE2 |
| | 8-iso-15-keto PGE2 |
| | 8-iso PGE2 isopropyl ester |

⇧indicates relative potency to increase HSC production. No arrow indicates insignificant HSC enhancement relative to control.

Figure 4A:
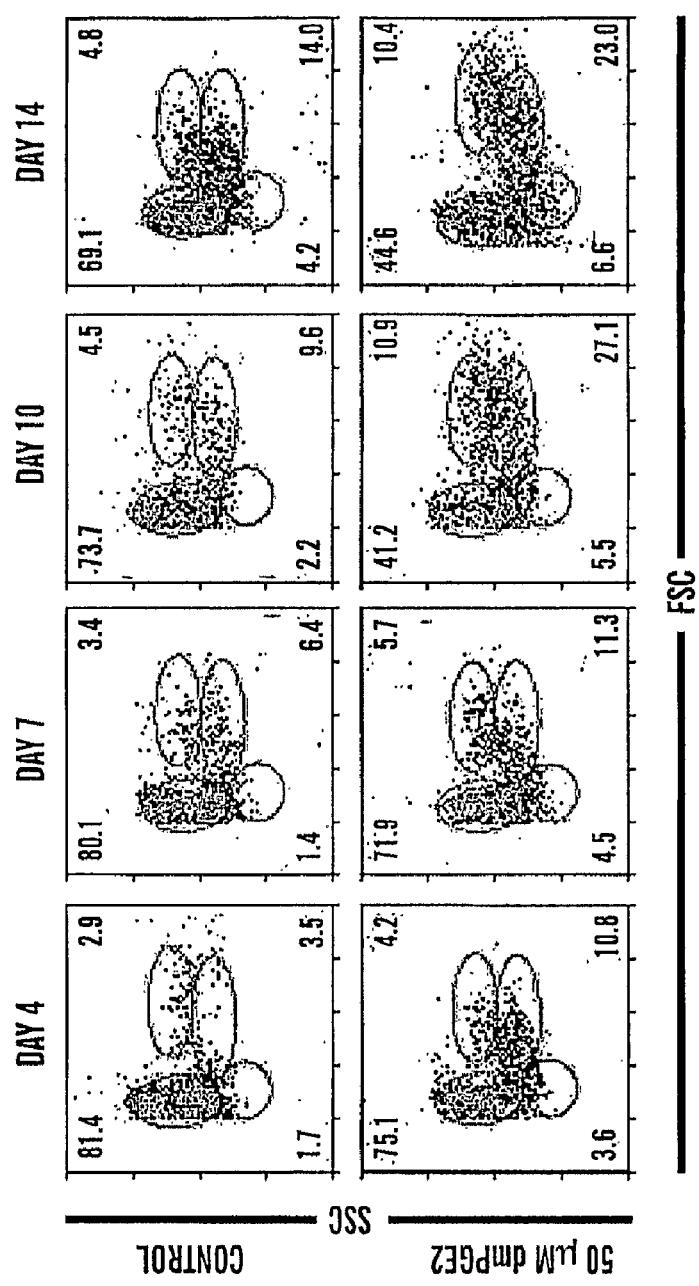
FIGS. 4A and 4B show that treatment with dmPGE2 enhances hematopoietic recovery in sublethally irradiated adult zebrafish. Zebrafish whole KM irradiation recovery experiments were performed. Asterisks (*) indicate statistically significant differences: *=50 μM vs control, =50 μM vs 10 μM and 50 μM vs control, *=all variables significant (ANOVA, p<0.05, n=15/variable).
Figure 4A:
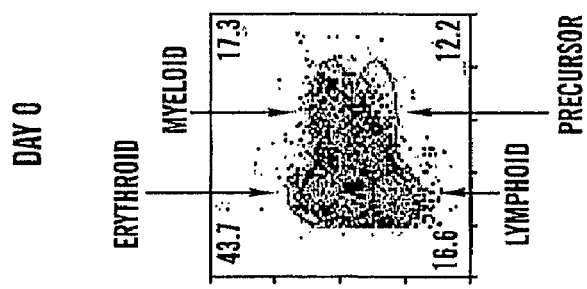
Figure 4B:
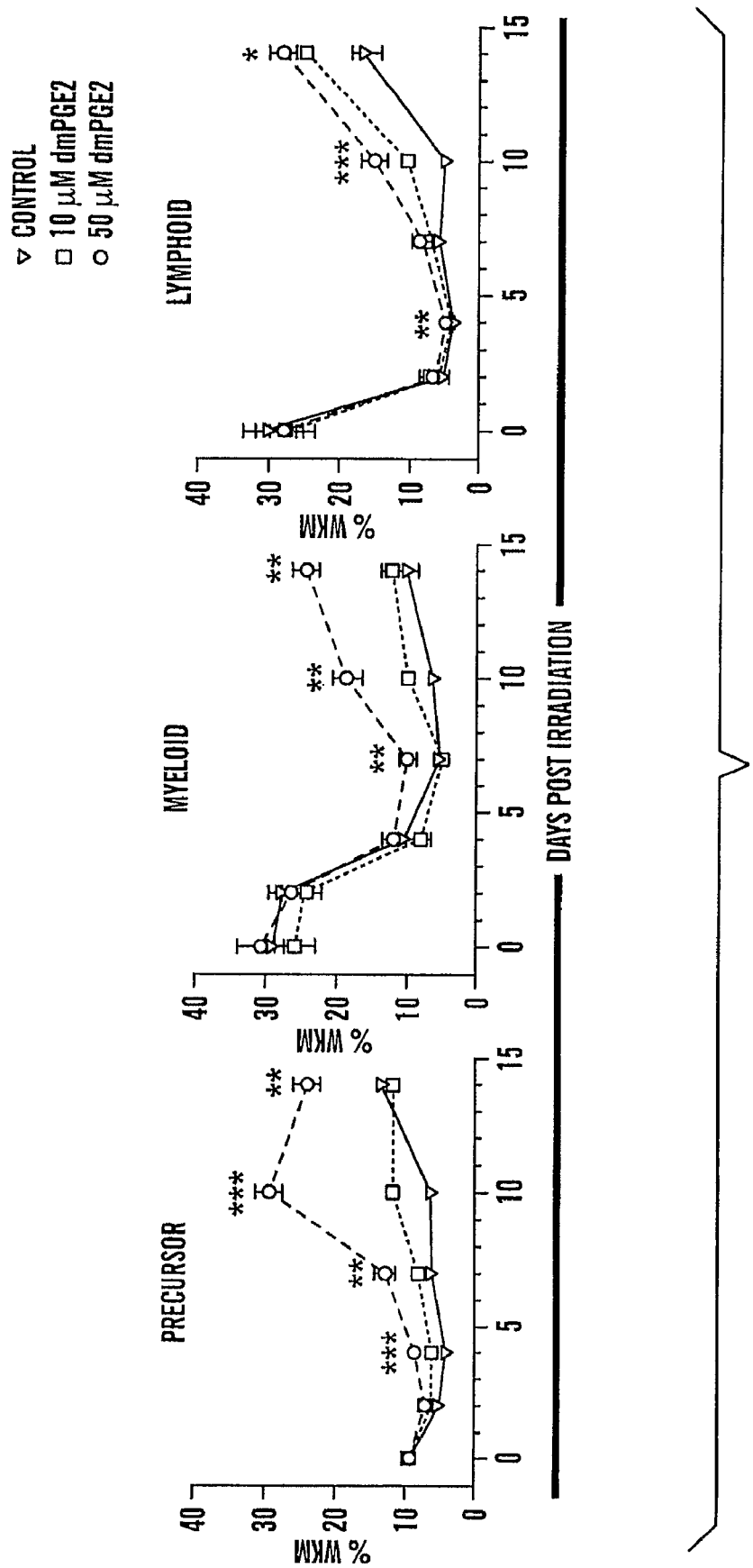
Figure 5A:
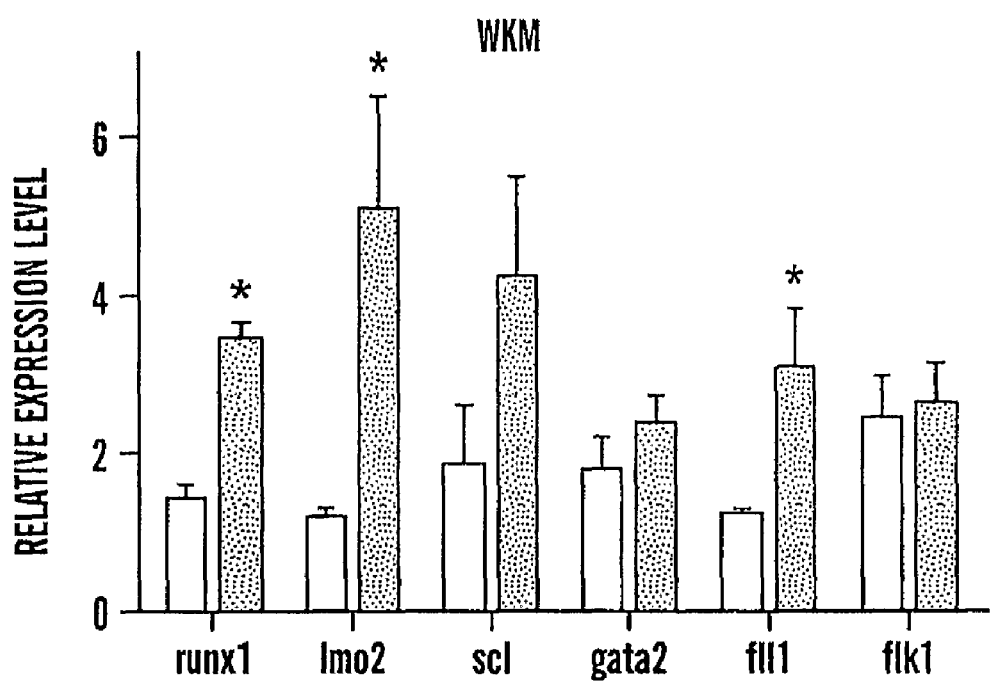
FIGS. 5A and 5B depict modulation of PG pathway that alters expression of HSC-related genes and recovery in sublethally irradiated adult zebrafish.
Figure 5B:
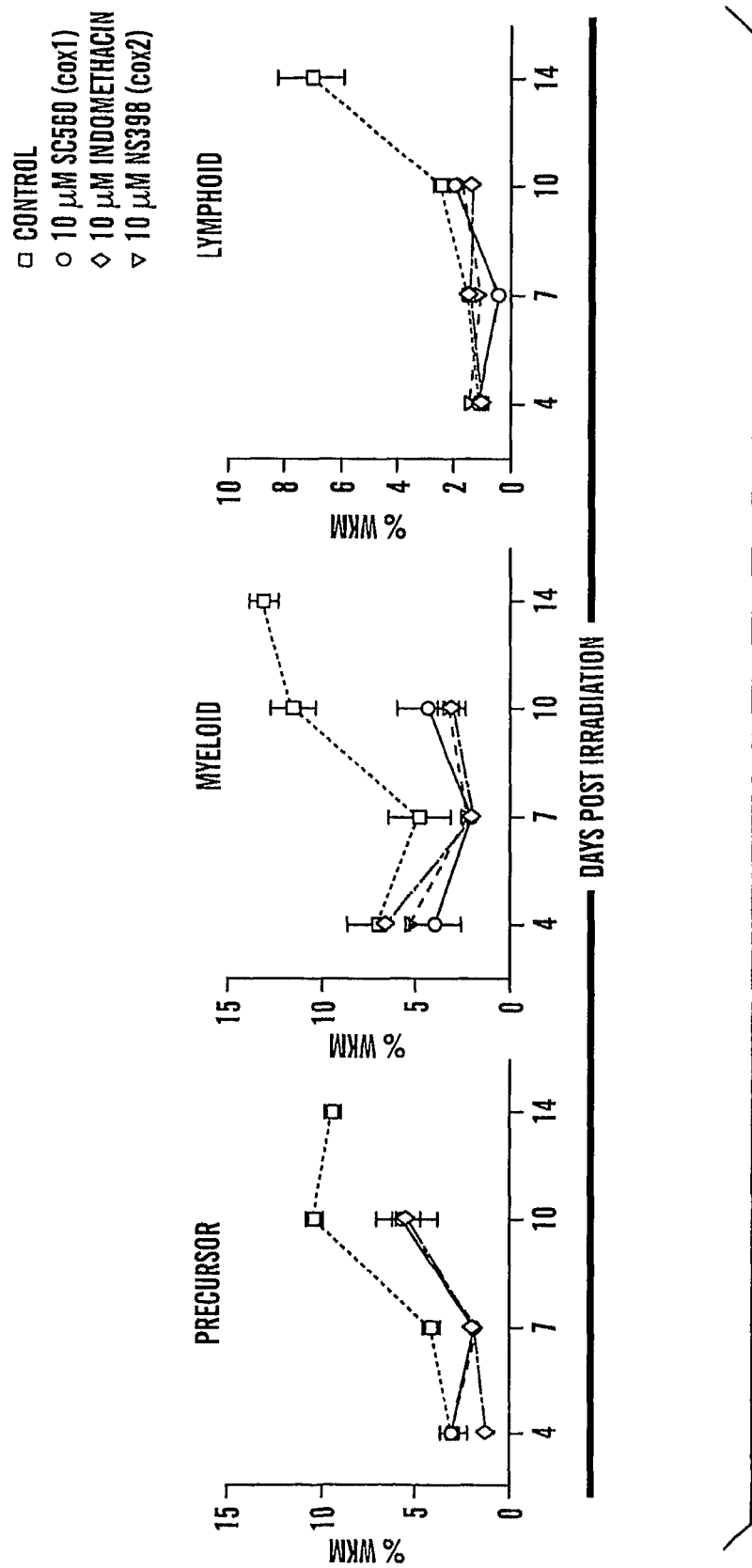

To examine the role of PGE2 in HSC homeostasis in adult zebrafish, a kidney marrow (KM) irradiation recovery assay was performed. Burns et al., 19 Genes & Devel. 2331-42 (2005). Wild-type fish were sublethally irradiated, exposed to dmPGE2, and evaluated for kinetics of KM recovery by FACS 11 (FIG. 4A). The rate of hematopoietic reconstitution of the KM was significantly enhanced in fish exposed to 50 μM dmPGE2 compared to DMSO-exposed controls (FIGS. 4A, B). The elevation in percentage of progenitors preceded recovery of the myeloid and lymphoid populations, respectively. The expression levels of stem, progenitor and endothelial cell markers by qPCR on PGE2-treated KM at day three post-irradiation showed significant upregulation of runx1 and lmo2 (FIG. 5). Inhibition of cox activity by non-selective and selective inhibitors significantly decreased KM recovery and affected overall survival (FIG. 5). Our results indicate that PGE2 plays an important role in KM homeostasis.

Figure 6A:
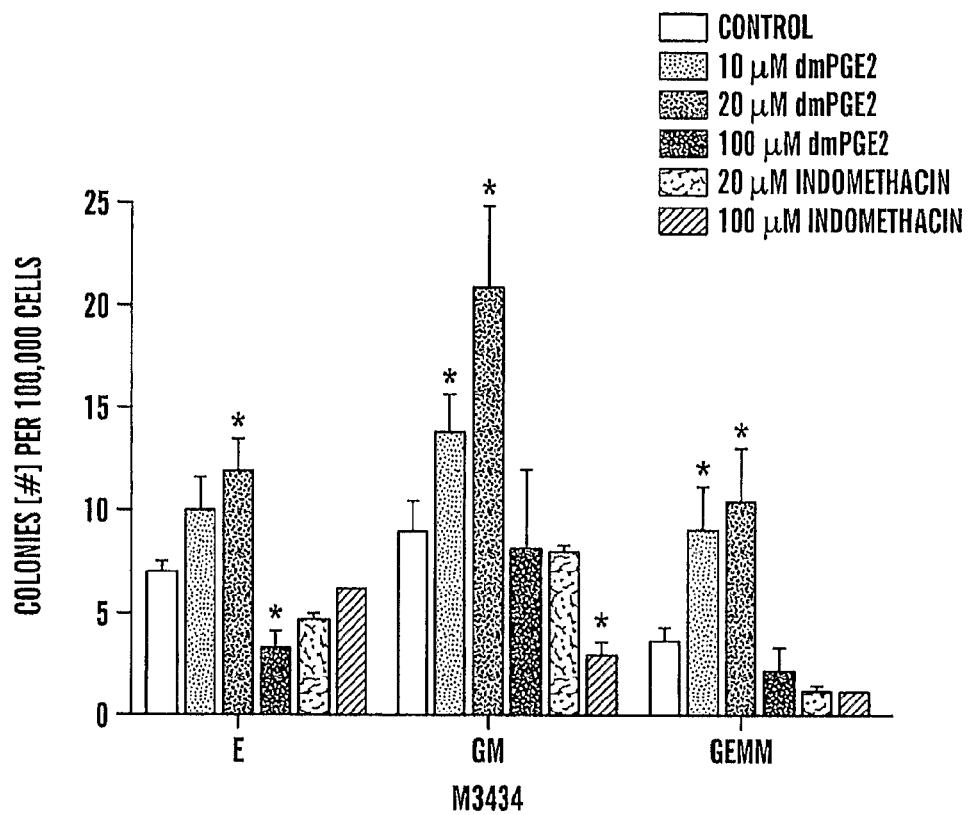
FIGS. 6A and 6B show that dmPGE2 modulates colony number and hematopoietic differentiation in mouse ES cells. M3434 and OP9 ES cell colony forming assays were performed; counts are per 100,000 cells plated. The bars indicate control-treated ES cells and treatment with increasing doses of dmPGE2 (10 μM, 20 μM, 100 μM) or indomethacin-treated (10 μM, 100 μM) ES cells. An asterisk (*) indicates a statistically significant difference (two-tailed t-test, n=5/variable).
Figure 6B:
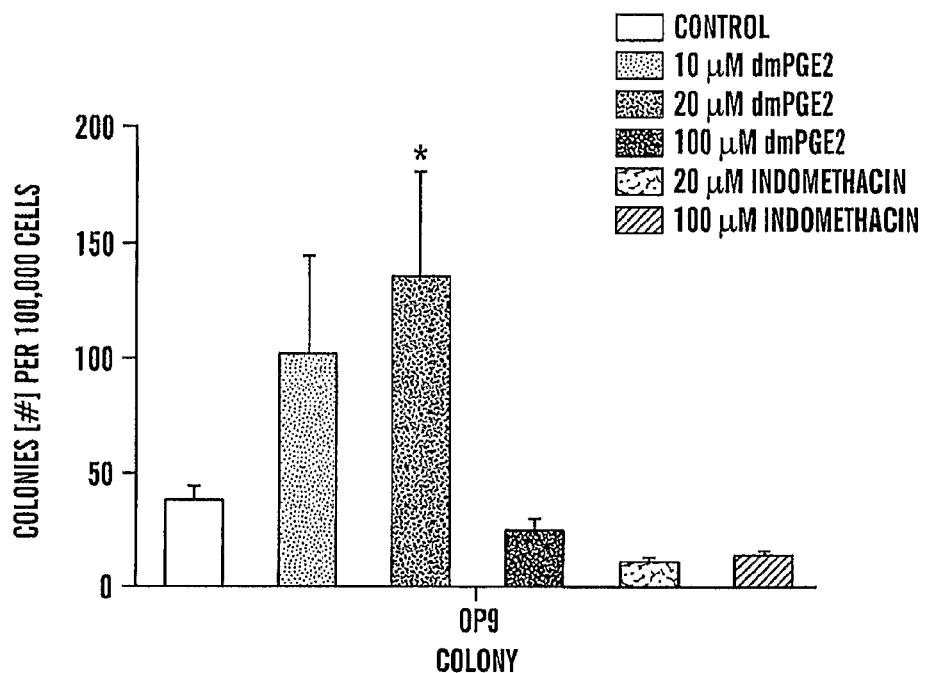
Figure 7A:
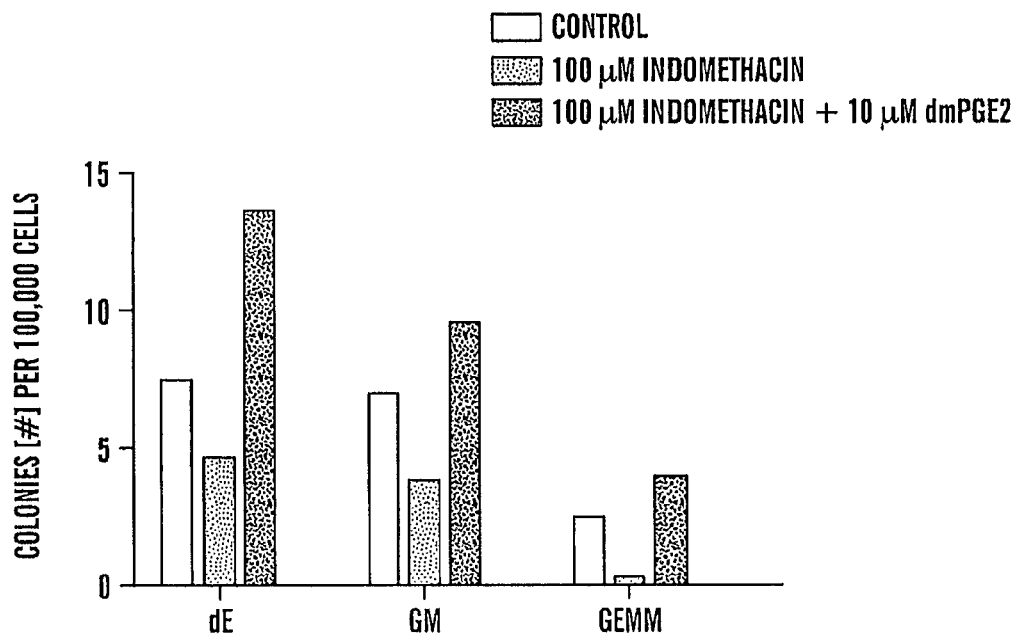
FIGS. 7A and 7B depict PGE2 influences on colony number. More specifically.
Figure 7B:
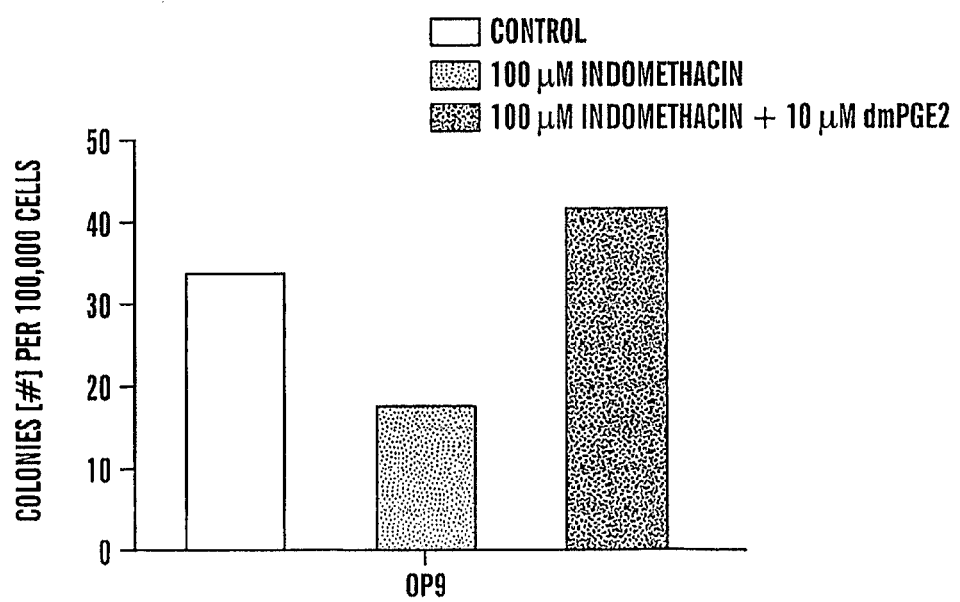

The effects of the prostaglandin pathway on mammalian HSC and progenitor populations were also evaluated. Addition of dmPGE2 to ES cells during embryoid body expansion increased hematopoietic colonies number on an OP9 stromal cell layer and in methylcellulose colony-forming assays (FIGS. 6A, B). Nakano et al., 272 Sci. 722-24 (2002). OP9, definitive erythroid (dE) and granulocyte/monocyte (GM) colonies increased in a dose-dependent manner after exposure to 10 μM (GM p=0.005) and 20 μM (OP9 p=0.047; dE p=0.04; GM p=0.007) dmPGE2. The number of multipotent granulocyte/erythrocyte/monocyte/macrophage (GEMM) colonies was enhanced 2.9-fold following dmPGE2 treatment (10 μM: p=0.017; 20 μM: p=0.016). At 100 μM, dmPGE2 was toxic to ES cells. qPCR was performed to determine if PG pathway components were present in ES cells: Cox1, Cox2, PGE2 synthase, and PGE receptors 1-4 were present at all stages examined. Indomethacin inhibited colony growth at 20 μM (OP9 p=0.047) and 100 μM (GM p=0.024) (FIGS. 6A, B); the inhibitory effects were rescued by exogenous dmPGE2 in both colony-forming assays (FIGS. 7A, B). These data suggest that the role of the prostaglandin pathway in hematopoiesis is conserved between zebrafish and mammals.

Alternatively, the expansion of hematopoietic or endothelial cells in the AGM (aorta-gonad-mesonephros) region may be studied by mating mice, then dosing newly pregnant females with PGE2 in their drinking water starting at day 8.5 of embryonic development. PGE2 levels may have an effect on implantation of murine embryos; waiting until day 8.5 to begin treatment allows implantation to proceed, yet still provides time for the drug to affect the stem cell population that can be found in the AGM region starting at day 10.5. Pregnant females are sacrificed with $CO_2$ at day 11.5 of embryonic development and embryos are isolated from the uterus and fixed with paraformaldehyde. Fixed embryos may be processed for whole mount in situ hybridization for markers of HSCs, such as Runx1, c-myb or Sca1, or subjected to immunohistochemistry with antibodies to HSCs to find evidence of an expanded stem cell population. Different doses, e.g., 10(−1), 10(−3) and 10(−5) micrograms/g body weight, may be used. Three pregnant female mice may be used for each dose noted above, and for an unexposed control variable. The effective dose is then used in transplantation experiments involving cells dissected from the AGM region of embryos.

Expansion of CFU-S and Long-term Repopulating HSCs may be studied in mice as well. The single dose of PGE2 found to expand potential stem cells in the AGM region may be fed to pregnant females following implantation (approx E8.5) in the drinking water. Control females are treated in parallel. Pregnant females are euthanized at 11.5 dpc. The embryos are collected from the uterus, the AGM region isolated by microdissection and AGM cells prepared for transplantation. A combination of one embryo equivalent of experimental and/or control cells will be injected into the tail vein of irradiated recipient mice, where they will home to the spleen (short term) and bone marrow (long term). The contribution of experimental cells versus control cells may be analyzed at twelve days post transplant by a standard CFU-S assay for spleen colony number of sacrificed recipient mice, or by flow cytometry of bone marrow at one month post-transplantation to determine competitive long-term HSC repopulation.

Because the development of the cardiovascular system is intimately linked to the production of hematopoietic stem cells during embryogenesis, the effect of blood pressure on PGE2 signaling and the induction of AGM HSCs may be relevant. The most conserved site for hematopoiesis in any vertebrate is the ventral wall of the aorta. The cells in the aorta arise at thirty hours of development in the zebrafish and develop there until about forty-six hours when they enter circulation or invade tissues. AGM HSC production may be timed to occur after the first heartbeat and when blood pressure within the vasculature reaches a critical level. In the zebrafish, the first heartbeat occurs at twenty-three hours. At this time, the heartbeat is slow and the contraction of the heart is relatively weak. At thirty hours, robust circulation is established. The cue to make AGM stem cells may be an alteration in blood pressure. Several chemicals identified in zebrafish screening regulate blood pressure and cardiac contractility. For example, the chemical hydralazine, a commonly used antihypertensive, is known to increase prostaglandin E2 expression. In situ analysis of embryos exposed to hydralazine demonstrates very few chances in angiogenesis, but a great increase in blood stem cell number. In addition, the drug strophanthidin, a cardiac glycoside, increases contractility of the heart and also increases AGM stem cells. Furthermore, the beta-blocker, atenolol, leads to vasodilation and also leads to a heightened production of AGM stem cells. Chemicals that perturb heart beat, such as BDM and epinephrine, as well as the silent heart mutant may alter the production of AGM stem cells, and may establish if circulation is necessary for AGM production. To further establish the relationship between blood pressure and the prostaglandin pathway, hydralazine, strophanthidin, and atenolol may be incubated with the zebrafish in the presence of COX2 inhibitors. Similar studies can be done with the COX2 morpholino to determine if they are able to block the activation of stem cells mediated by hydralazine.

Figure 8B:
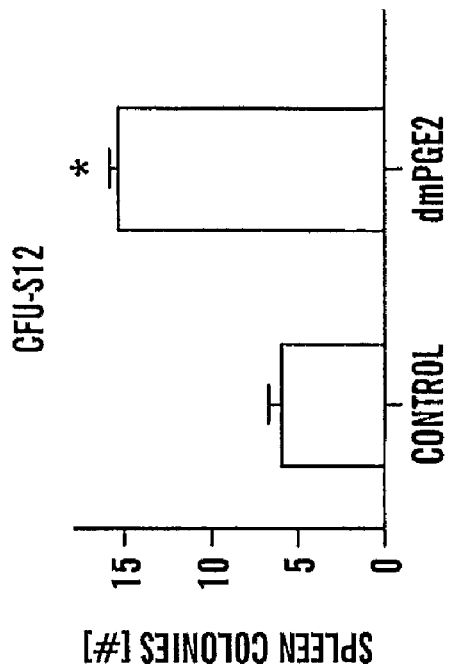
FIG. 8A-FIG. 8F indicate that exposure of murine BM to dmPGE2 increases the number of CFU-S and repopulating HSCs. An asterisk (*) indicates a statistically significant difference.
Figure 8A:
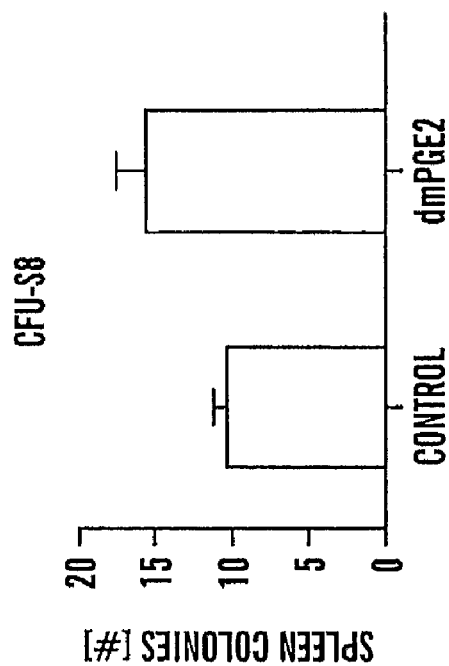
Figure 8D:
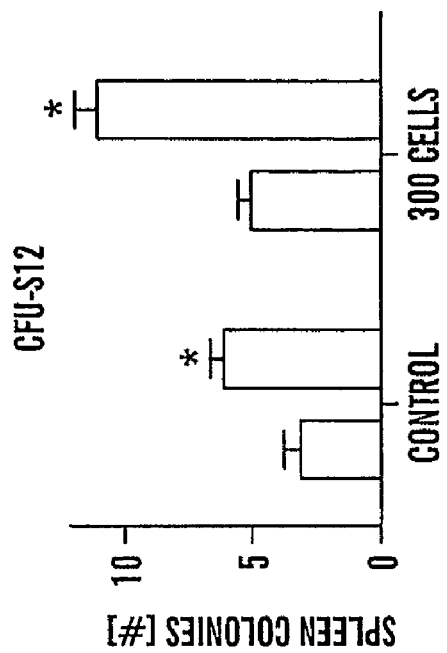
Figure 8C:
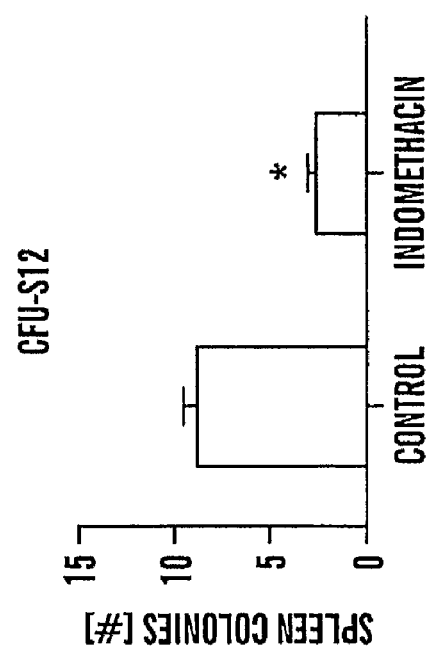
Figure 9B:
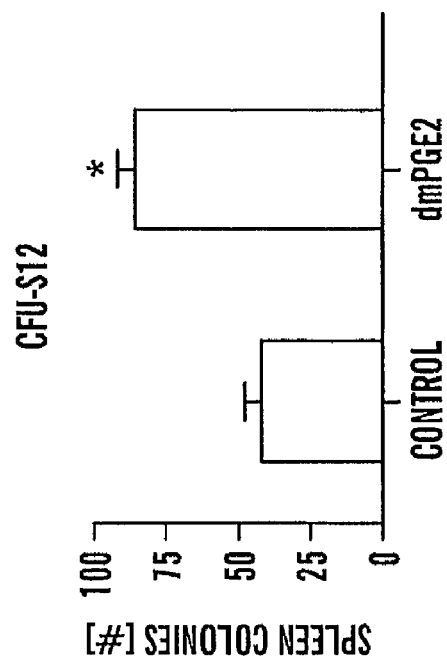
Figure 9A:
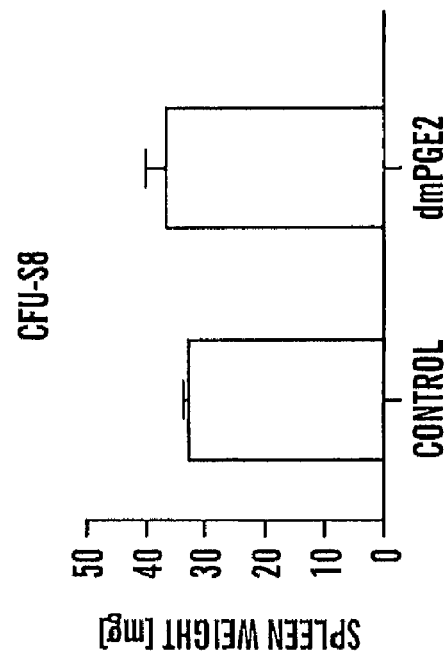
FIGS. 9A-9N depict data showing that exposure of murine BM to dmPGE2 increases spleen weight and 1 HSC engraftments.
Figure 9D:
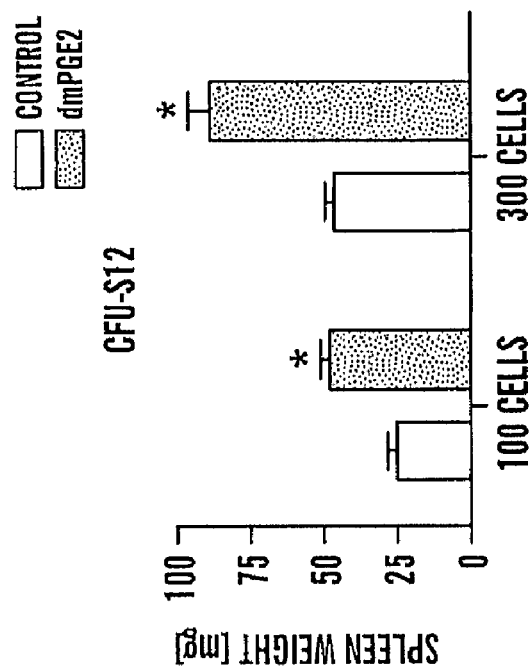
FIG. 9D, Spleen colony number after dmPGE2 treatment of KSL cells (two-tailed t-test, 100 cells: n=4, p=0.0013; 300 cells: n=5, p=0.009).
Figure 9C:
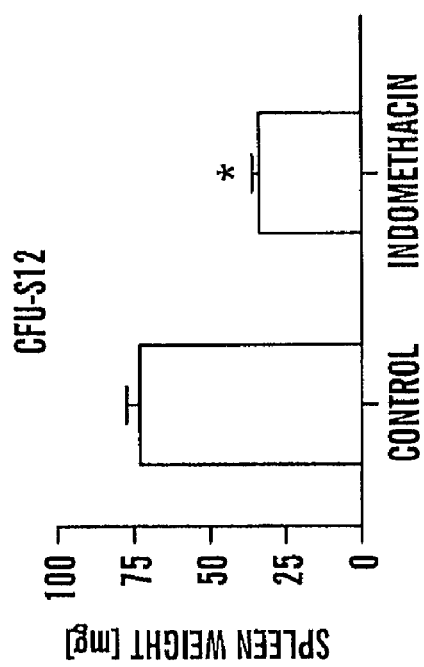
FIG. 9C, Splenic weight following indomethacin treatment (green) compared to control (two-tailed t-test: n=10, p=0.00026).
Figure 9E:
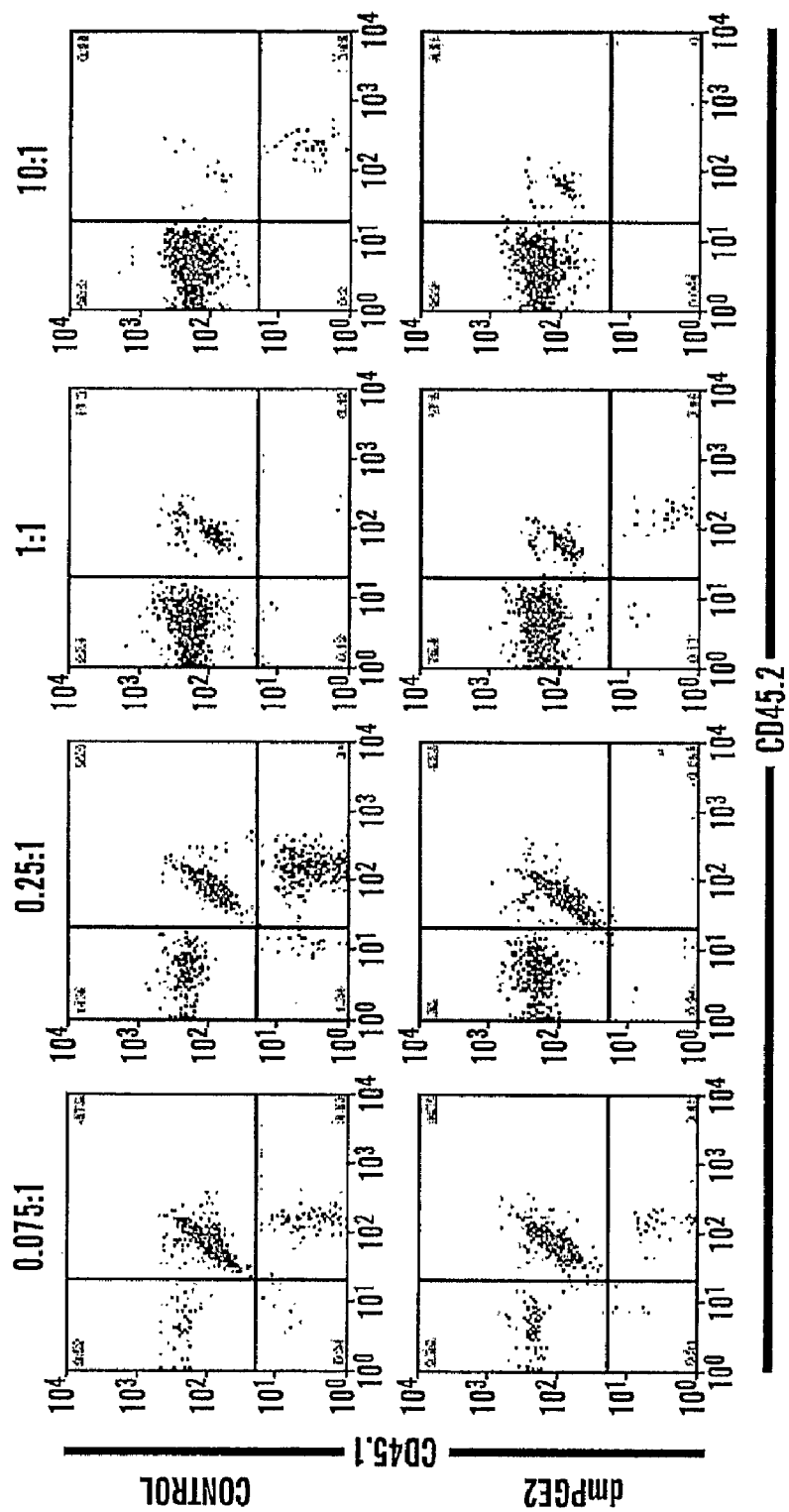
FIG. 9E, Representative FACS plots illustrating the levels of CD45.1 engraftment (upper left quadrant) in recipients of control and dmPGE2 exposed BM cells.
Figure 9G:
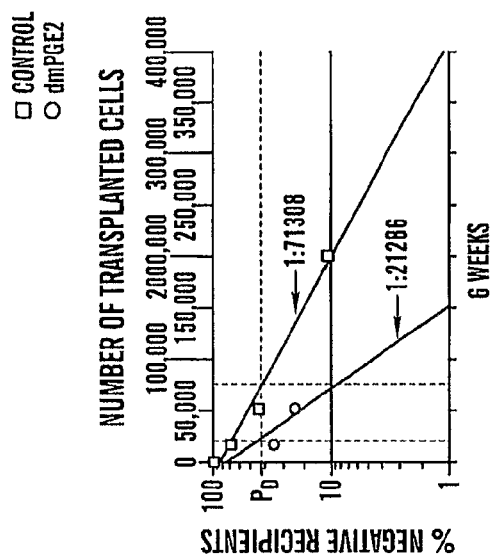
FIGS. 9F-9J, Average chimerism (F, H, I) and calculated frequency of engraftment (FIGS. 9G and 9J) in recipients of dmPGE2-treated WBM (circles) versus control (squares).
Figure 9F:
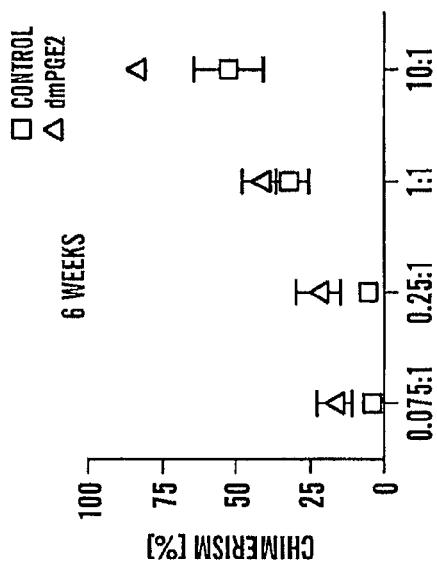
Figure 9H:
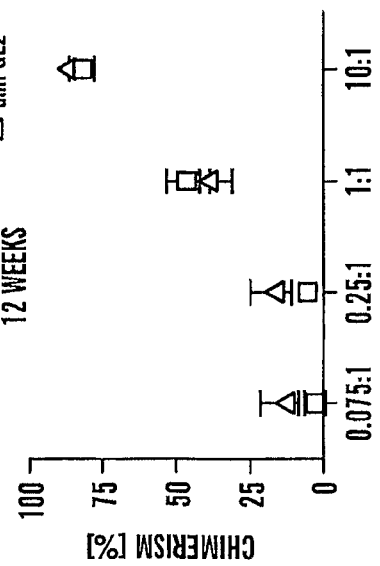
Figure 9J:
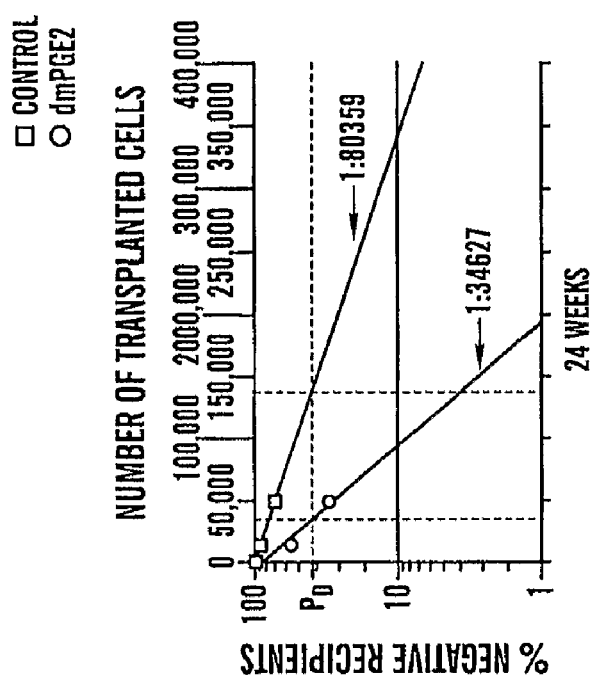
Figure 9I:
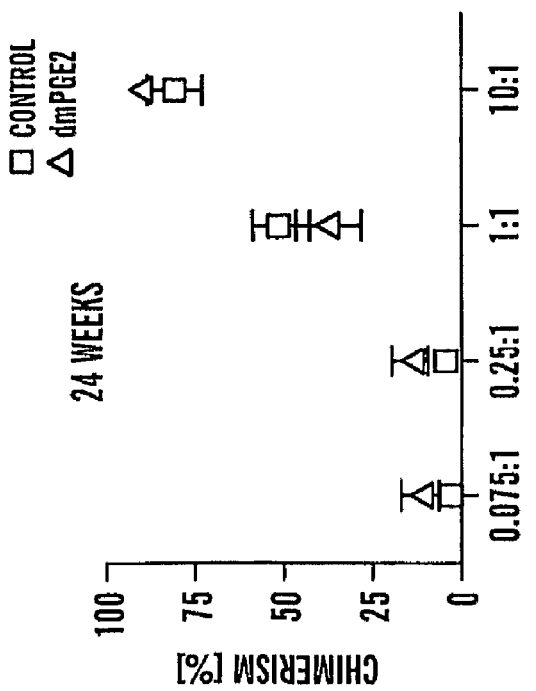
Figure 9L:
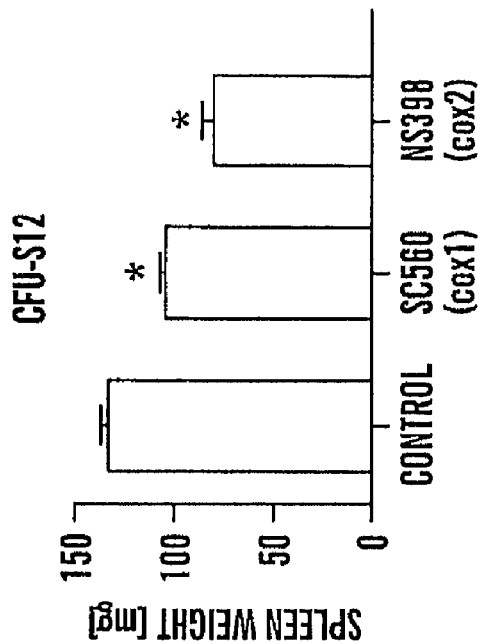
FIGS. 9K and 9L, Effect of ex vivo treatment of WBM with cox1 (SC560, 10 μM) and cox2 (NS398, 10 μM) inhibitors in the CFU-$S_{12}$ assay on colony number (paired t-test, n=10, SC560 p=0.00016, NS398 p<0.00001 and splenic weight paired t-test, n=10, SC560 p=0.025, NS398 p=0.00075).
Figure 9K:
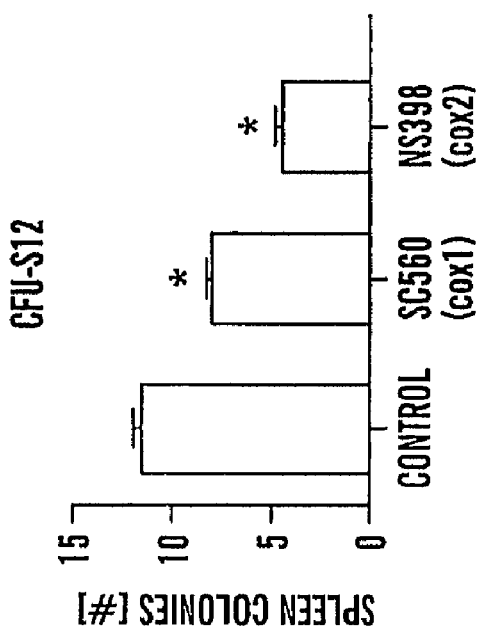
Figure 9N:
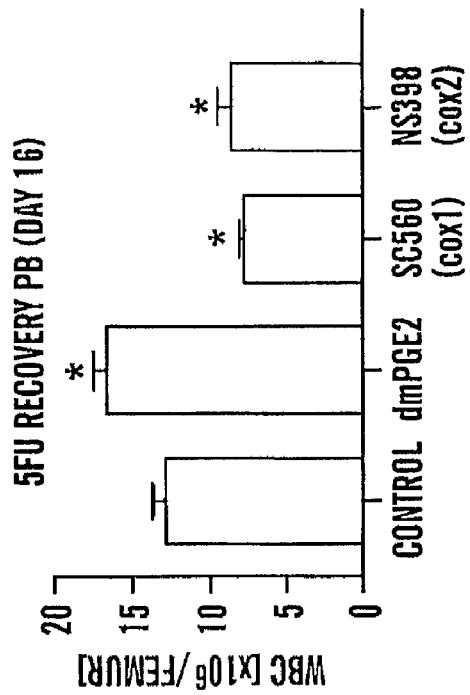

To explore potential in vivo effects, murine whole bone marrow (WBM) was exposed ex vivo to dmPGE2 (1 μM/106 cells) and irradiated recipients were transplanted with $6 \times 10^4$ treated WBM cells. The number of CFU-S12 was increased three-fold (p<0.0001) in recipients of dmPGE2-treated WBM (FIG. 8b, FIG. 9A, Table 6-Table 8); similarly, more mature CFU-S8 colonies were also enhanced (FIG. 9A, Table 5). To assess the endogenous PGE2 requirement, WBM cells were incubated ex vivo with indomethacin (1 μM/106 cells). After transplantation of $1 \times 10^5$ cells, a 70% decrease (p=0.0002) in the number of CFU-S12 was observed in recipients of indomethacin-treated cells (FIG. 8C, FIG. 9C, Table 4-Table 6); similar results were seen with specific cox1 and cox2 inhibition (FIGS. 9K, L). These results suggest that PGE2 treatment not only enhances hematopoietic stem cell formation, but is required for CFU-S activity.

TABLE 5

Effect of dmPGE2 on CFU-S$_{12}$

| Ex vivo Treatment | Murine Cell Population | # Cells Transplanted | CFU-S$^{12}$ (n + 10) Weight mg Ave (SD) | Colony Number |
|---|---|---|---|---|
| EtOH | Whole Marrow | 6000 | 41.9 (15.8) | 5.8 (2.6) |
| dmPGE2 | Whole Marrow | 6000 | 85.4 (16.5) | 15.2 (2.2) |
| EtOH | Whole Marrow | 100000 | 71.8 (18.1) | 8.8 (2.1) |
| Indomethacin | Whole Marrow | 100000 | 32.7 (8.7) | 2.5 (1.4) |
| EtOH | Kit+Sca+Lin− | 100 | 25.1 (5.9) | 3.0 (1.4) |
| dmPGE2 | Kit+Sca+Lin− | 100 | 47.7 (5.6) | 6.2 (1.2) |
| EtOH | Kit+Sca+Lin− | 300 | 46.1 (5.6) | 5.0 (1.1) |
| dmPGE2 | Kit+Sca+Lin− | 300 | 88.2 (14.8) | 11.0 (1.7) |

Spleen weight and CFU-S activity was assessed at day twelve in irradiated recipients injected with either WBM or ckit+sca1+lineage− FACS sorted cells treated with EtOH, dmPGE2 or indomethacin (1 μM/10$^6$ cells).

TABLE 6

Effect of dmPGE2 on radio-protective competitive BM repopulation.

| Ex vivo Treatment | CD45.1 Test Cell Dose | CD45.1/2 Competitor Cell Dose | 6 wk CD45.1 Engraftment | | CD45.2 |
|---|---|---|---|---|---|
| | | | Animals with >5% CD45.1 | Mean % CD45.1 chimerism (±SD) | Recipients Analyzed Total |
| EtOH | 15000 | 200000 | 3 | 4.0 ± 7.8 | 10 |
| | 50000 | 200000 | 4 | 5.8 ± 5.7 | 8 |
| | 200000 | 200000 | 9 | 32.5 ± 20.7 | 10 |
| | 2000000 | 200000 | 9 | 52.4 ± 34.8 | 9 |
| dmPGE2 | 15000 | 200000 | 7 | 16.9 ± 19.5 | 10 |
| | 50000 | 200000 | 8 | 22.7 ± 24.2 | 10 |
| | 200000 | 200000 | 10 | 41.9 ± 17.2 | 10 |
| | 2000000 | 200000 | 10 | 85.1 ± 3.1 | 10 |

WBM (CD45.1) was treated ex vivo with EtOH vehicle or dmPGE2 and transplanted into sublethally irradiated recipients (CD45.2) with a fixed number of (CD45.1/CD45.2) competitor cells at the ratios shown in columns 2 and 3. Column 4 illustrates the number of animals with more than 5% CD45.1 chimerism at six weeks, and column 5 demonstrates the mean percentage of chimerism. The last column indicates the number of CD45.2 recipients analyzed.

TABLE 7

Effect of dmPGE2 on radio-protective competitive BM repopulation.

| | | | 12 wk CD45.1 Engraftment | | CD45.2 |
|---|---|---|---|---|---|
| Ex vivo Treatment | CD45.1 Test Cell Dose | CD45.1/2 Competitor Cell Dose | Animals with >5% CD45.1 | Mean % CD45.1 chimerism (±SD) | Recipients Analyzed Total |
| EtOH | 15000 | 200000 | 2 | 1.9 ± 2.9 | 9 |
| | 50000 | 200000 | 3 | 5.4 ± 4.4 | 8 |
| | 200000 | 200000 | 10 | 46.9 ± 22.9 | 10 |
| | 2000000 | 200000 | 10 | 82.8 ± 14.1 | 9 |
| dmPGE2 | 15000 | 200000 | 5 | 15.1 ± 22.2 | 10 |
| | 50000 | 200000 | 8 | 18.1 ± 22.2 | 10 |
| | 200000 | 200000 | 10 | 40.8 ± 28.7 | 10 |
| | 2000000 | 200000 | 10 | 87.8 ± 4.0 | 10 |

WBM (CD45.1) was treated ex vivo with EtOH vehicle or dmPGE2 and transplanted into sublethally irradiated recipients (CD45.2) with a fixed number of (CD45.1/CD45.2) competitor cells at the ratios shown in columns 2 and 3. Column 4 illustrates the number of animals with more than 5% CD45.1 chimerism at twelve weeks, and column 5 demonstrates the mean percentage of chimerism. The last column indicates the number of CD45.2 recipients analyzed.

TABLE 8

Effect of dmPGE2 on radio-protective competitive BM repopulation.

| | | | 24 wk CD45.1 Engraftment | | CD45.2 |
|---|---|---|---|---|---|
| Ex vivo Treatment | CD45.1 Test Cell Dose | CD45.1/2 Competitor Cell Dose | Animals with >5% CD45.1 | Mean % CD45.1 chimerism (±SD) | Recipients Analyzed Total |
| EtOH | 15000 | 200000 | 1 | 1.9 ± 2.5 | 9 |
| | 50000 | 200000 | 2 | 4.7 ± 4.2 | 7 |
| | 200000 | 200000 | 10 | 51.18 ± 26.3 | 10 |
| | 2000000 | 200000 | 9 | 81.7 ± 24.4 | 9 |
| dmPGE2 | 15000 | 200000 | 4 | 10.2 ± 10.3 | 9 |
| | 50000 | 200000 | 7 | 14.3 ± 16.6 | 10 |
| | 200000 | 200000 | 10 | 39.1 ± 31.0 | 10 |
| | 2000000 | 200000 | 10 | 90.7 ± 4.0 | 10 |

WBM (CD45.1) was treated ex vivo with EtOH vehicle or dmPGE2 and transplanted into sublethally irradiated recipients (CD45.2) with a fixed number of (CD45.1/CD45.2) competitor cells at the ratios shown in columns 2 and 3. Column 4 illustrates the number of animals with more than 5% CD45.1 chimerism at twenty-four weeks, and column 5 demonstrates the mean percentage of chimerism. The last column indicates the number of CD45.2 recipients analyzed.

The PG pathway components are present in both stromal cell and HSC populations in mice and humans (Princeton Stem Cell and Stromal cell databases). Ivanova et al., 298 Sci. 601-04 (2002); Nakano et al., 101 Blood 383-89 (2003). Cox1, Cox2, PGE2-synthase and receptors EP2 and EP4 are present in fetal liver HSCs and in BM HSC after 5-fluorouracil (5FU) injury, suggesting PGE2 signaling is utilized by HSCs. Venezia et al., PLoS Biol 2, e301 (2004). To determine if the increase in CFU-S number is due to a direct effect of PGE2 on the stem cell population, FACS-isolated ckit+sca1+ lineage-(KSL) BM cells were exposed to dmPGE2 and transplanted at 100 or 300 cells per irradiated recipient. Both splenic weight (FIG. 9D) and CFU-S12 were significantly increased in recipients of dmPGE2-treated cells (FIG. 9D, Table 6-Table 8). These results indicate that dmPGE2 can lead to cell autonomous activation of HSCs and immature progenitors.

Figure 8F:
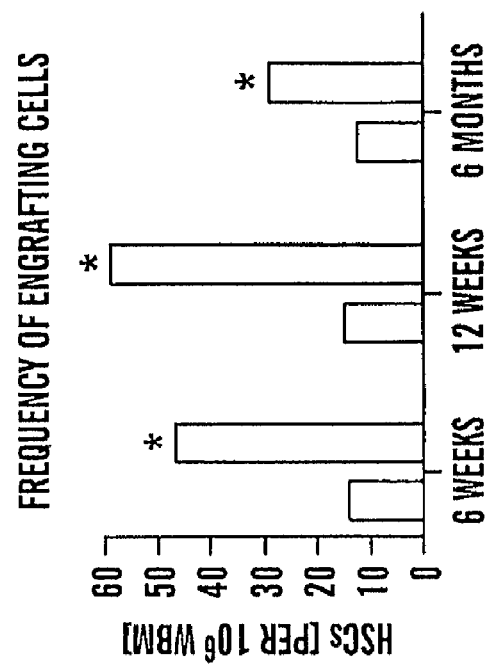
Figure 8E:
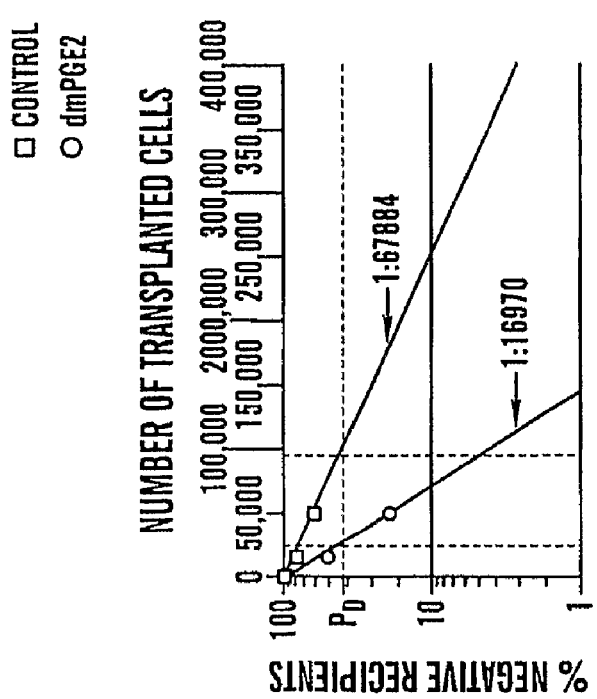

To determine whether dmPGE2 exposure can enhance HSC reconstitution, limiting dilution competitive repopulation analysis was conducted. Zhang & Lodish, 103 Blood 2513-21 (2004). WBM (CD45.1) exposed to dmPGE2 ex vivo was mixed independently at varying doses with a fixed number of untreated competitor cells (CD45.1/CD45.2) and injected into congenic recipient mice (CD45.2). Peripheral blood was obtained at six, twelve, and twenty-four weeks post-transplantation and examined by FACS to determine the contribution of treated-test cells to hematopoietic repopulation (FIGS. 9E-9J). Positive reconstitution was defined as test cell multi-lineage chimerism >5% (FIGS. 9F, H, I). A significant increase in the number of repopulating cells as determined by Poisson statistical analysis was seen in dmPGE2-treated BM (FIG. 8E, FIGS. 9G, 9J). At six weeks, the calculated frequency of engraving cells per 106 WBM cells was enhanced 3.3-fold (p=0.005) in the recipients of dmPGE2-treated WBM, and the frequency of short-term repopulating HSCs was 4-fold (p=0.002) higher at twelve weeks post-transplant (FIGS. 8E, 8F, FIG. 9G). At twenty-four weeks, the frequency of long-term repopulating HSCs was 2.3-fold enhanced (p=0.05) in recipients of dmPGE2-treated cells (FIG. 8F, FIG. 9J). At both the twelve- and twenty-four-week analyses, reconstitution in all recipients was multilineage, indicating that transient dmPGE2 treatment increased the frequency of repopulating HSCs in the mouse without impairing differentiative capacity. No decline in the contribution of dmPGE2-treated HSCs to hematopoiesis was observed. To determine whether dmPGE2 treatment enhanced homing to the BM niche, WBM was labeled with a vital dye, CDFA, then exposed to dmPGE2 and transplanted. At twelve hours post-transplantation, there was no significant difference in homing between the control and dmPGE2-treated cells (p=0.83).

In an effort to more precisely characterize the requirement of the prostaglandin pathway in stem cell production, several additional commercially available cyclooxygenase (COX)

inhibitors were utilized. General COX inhibitors indomethican, naproxen, ibuprofen, and asprin, as well as the Cox2 specific inhibitor NS-398, were all tested for effects on AGM HSCs via the assay described above. Each Cox1 or Cox2 chemical inhibitor reduced stem cells in the aorta. Cox is responsible for processing PG's by altering arachadonic acid. Vasculogenesis and aorta specification remained intact in treated embryos as seen by ephrinB2 and Flk1 staining, however some aspects of angiogenesis, particularly the morphology of the inter-somitic blood vessels, were perturbed by some of the chemicals. Morpholino antisense oligonucleotides for COX1 and COX2 were also injected individually into zebrafish embryos to confirm that the reduction of stem cells in the aorta was due to Cox inhibition. Runx1+Cmyb+ cells were reduced in AGM region with either morpholino. As reported previously, very high concentrations of the Cox1 MO caused defects in the specification of the aorta and vein, while the cox2 morpholino caused a gastrulation arrest at high concentrations. Cha et al., 20 Genes & Devel. 77-86 (2006); Cha et al., 282 Devel. Biol. 274-83 (2005). The reduction in HSCs was observed at lower concentrations of either MO, and the vessel structures in the tail were not severely altered. Additionally, fli1 GFP transgenic zebrafish that precisely delineate the vasculature were used to evaluate the effect of the morpholinos and chemicals on angiogenesis. In hybridization of Cox 1 or Cox2 does not affect development of the aorta by chemicals or morpholinos. Intersomitic blood vessels are altered by some treatments.

Prostaglandin E2 is the major prostaglandin that is made during zebrafish embryogenesis and regulates vascular tissues. Pini et al., 25 Arterioscler Thromb Vasc Biol. 315-20 (2005); Grosser et al., 99 P.N.A.S. USA 8418-23 (2002). Precisely which prostaglandins are effected by both chemical and/or morpholino inhibition of prostaglandin pathway components may be analyzed by mass spectroscopy analysis. Similarly, mass spectroscopy may confirm E2 induction following exposure to prostaglandin pathway substrates such as lineolic acid or mead acid. The analysis of the role of PGE2 in the formation of AGM HSCs logically leads to analysis of which receptors are active in propagating prostaglandin signaling to downstream effectors. Four PGE2 receptors have been identified in the zebrafish. Specific agonists and antagonists of the PGE receptors assist in this identification. Additionally the specific receptors that are mediating HSC induction can be studied by functional knockdown using morpholinos as described earlier. The expression of each of the prostaglandin receptors, as well as both cyclooxygenases may studied by in situ hybridization to evaluate the localization of these gene products throughout development, particularly focusing on the AGM region.

The present invention demonstrates that PGE2 enhances the number of hematopoietic stem cells and multipotent progenitors in two vertebrate species, zebrafish and mice. Prior studies have documented that unmodified PGE2 can affect blood cell maturation in the mouse (Boer et al., 100 Blood 467-73 (2002); Rocca et al., 99 P.N.A.S. USA 7634-39 (2002)), and the stimulation of cell cycle in CFU-S8 progenitors (Feher & Gidali, 247 Nature 550-551 (1974)); the effects of PG-mediated cell signaling on HSCs have not been examined previously, however. cox1 and cox2 appear to have distinct functions in AGM HSC formation; cox1 is important in the formation of the hematopoietic niche, particularly the hemogenic endothelium, while cox2 is likely involved in the self-renewal and proliferation of HSCs themselves. Conversely, homozygous Cox1 or Cox2 knockout mice are viable with no apparent defects in HSC formation (Langenbach et al., 58 Biochem. Pharmacol. 1237-46 (1999)); this is believed to be due to maternal and sibling contribution of PGE2. Cha et al., 282 Devel. Biol. 274-83 (2005); Langenbach et al., 83 Cell 483-92 (1995).

Figure 9M:
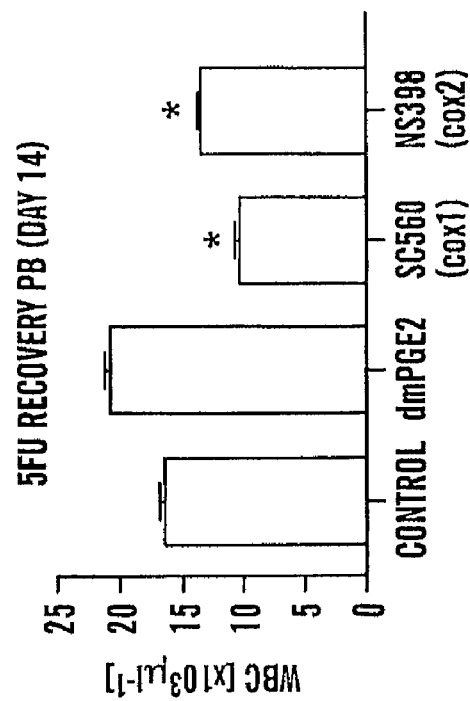

Significantly, analyses of Cox2-/- mice demonstrated alterations in hematocrit levels and an inability to recover from 5-FU induced BM injury (Lorenz et al., 27 Exp. Hematol. 1494-502 (1999); these findings imply the presence of HSC defects in adult Cox2-/- mice compatible with our proposed role for PG in HSC homeostasis. To clarify the roles of Cox1 and Cox2 in regulating HSC homeostasis in the adult, we performed a CFUS12 (FIGS. 9*k,l*) and 5-FU bone marrow recovery assay using selective chemical inhibitors of either cox1 (SC560) or cox2 (NS398). Inhibition of either enzyme was found to significantly alter CFUS activity, as well as the recovery of peripheral blood and BM WBC numbers (FIGS. 9*m,n*) compared to controls. Additionally, administration of dmPGE2 following 5FU treatment significantly enhanced BM recovery. Together, these data suggest that both Cox1 and Cox2 maintain a role in regulating HSC homeostasis in the adult mouse, as in the zebrafish, and that PGE2 is the mediator of this HSC regulation.

Patients undergoing BM transplantation display increased endogenous PGE2 levels. Cayeux et al., 12 Bone Marrow Transplant 603-08 (1993). Although cox inhibitors are not generally given post transplant because of platelet inhibition, our studies raised the possibility that administration of such agents following human BM transplantation might impair HSC engraftment. PGE2 and its analogues have been administered safely to humans. Talosi et al., 32 J. Perinat. Med. 368-74 (2004); Thanopoulos et al., 146 Eur. J. Pediatrics 279-82 (1987). These may be useful for ex vivo or in vivo expansion of HSCs. The concentration of dmPGE2 used to expand murine HSCs falls within the physiological range of PGE2 in human serum. Hertelendy et al., 3 Prostaglandins 223-37 (1973). The present disclosure illustrates that PGE2 functions as a potent regulator of HSCs in vertebrates, and may prove useful in treating patients with bone marrow failure or following transplantation.

The study of hematopoiesis in zebrafish has previously focused on the first wave of hematopoiesis, termed primitive, and the derivation of definitive hematopoietic stem cells in the aorta, gonads and mesonephros (AGM) region of the zebrafish embryo. Little is known about the production of AGM stem cells in vertebrates, but both runx1 and notch1 have been shown to be required for AGM HSC formation. There is also a genetic relationship whereby notch regulates runx1. A large scale chemical genetic screen for effectors of stem cell induction using a library of about 2500 compounds with known action indicated that chemicals that led to the production of prostaglandin (PG)E2 caused an increase in stem cell number, whereas chemicals that prevented PGE2 synthesis led to a reduction of stem cells. Other chemicals such as vasodilators and vasoconstrictors were also found to alter stem cell number, establishing a hypothesis that vascular tone during embryogenesis is a trigger for stem cell production. Members of the Wnt signaling pathway have been hypothesized to regulate hematopoietic stem cell numbers, although to date these studies have exclusively examined adult bone marrow homeostasis. The role of Wnt signaling in embryonic AGM production to identify potential genetic interactions with the notch-runx pathway, or with the prostaglandins, is investigated. To define additional genes that participate in AGM stem cell formation, a large-scale screen for mutants with defects in AGM production continues. At least twelve mutants have been isolated. The genes and pathways identified may have a significant impact on our understanding of basic stem cell biology, and could lead to new therapies for diseases such as sickle cell anemia, thalessemia, and aplastic anemia.

Approaches to characterizing the signaling pathways involved in definitive hematopoietic stem cell derivation during embryogenesis, using the zebrafish as a model, include evaluating the hypothesis that prostaglandins regulate AGM stem cell production using mutants, morphants, transgenics and chemicals and examining the role of the wnt pathway in the formation of AGM HSCs and investigate potential interactions with other signaling pathways known to be active in the AGM region. Zebrafish genetics may be used to define new pathways involved in AGM HSC formation during embryogenesis and allow for large-scale mutagenesis screens for defects in definitive hematopoiesis in zebrafish. This allows for the isolation and characterization of some of the mutated genes responsible for normal AGM HSC production.

Work in defining new pathways regulating the production of embryonic hematopoiesis has shed light on the CDX-HOX Pathway. It was discovered that the defective gene responsible for the decreased number of HSCs in the mutant zebrafish kugelig. Davidson et al., 425 Nature 300-06 (2003). The kgg mutant has a deficit of SCL+hematopoietic stem cells during early embryogenesis and lacks expression of the progenitor markers, GATA-1 and runx1. The vasculature in mutant embryos forms normally, but very few red cells circulate in the vasculature. The mutated gene encoded CDX4, a member of the caudal family. Mammals have three CDX genes including CDX1, 2, and 4. Caudal genes are known to act by regulating the HOX genes. The posterior HOX genes showed decreased expression in kgg mutants. It has been established that HOX genes act downstream of CDX4 in the development of blood. Overexpression of hoxb7 or hoxa9 led to a robust rescue of the hematopoietic defect in kgg mutants. To evaluate whether CDX4 is sufficient to specify the hematopoietic stem fate during embryogenesis, CDX4 mRNA was injected into zebrafish embryos. A number of SCL positive cells were found in regions of the embryo that normally would not form blood. The fact that cdx4 is sufficient to induce ectopic blood stem cells allows this work to translate into the mammalian system.

Despite the significant in vitro blood-forming potential of murine embryonic stem cells (ESCs), deriving hematopoietic stem cells (HSCs) that can reconstitute irradiated mice has proven to be challenging. Researchers have successfully engrafted lethally irradiated adult mice with ESCs engineered to ectopically express hoxB4. Kyba et al., 109 Cell 29-37 (2002). Blood reconstitution showed a myeloid predominance, likely due to an inability to fully pattern the adult HSC from these embryonic populations. Co-expression of CDX4 and hoxb4 promotes robust expansion of hematopoietic blasts on supportive OP9 stromal cultures. When injected intravenously into lethally-irradiated mice, these cell populations provide robust radio-protection, and reconstitute high-level lymphoid-myeloid donor chimerism. Wang et al., 102 P.N.A.S. USA 1981-86 (2005).

To explore pathways that could be downstream of the cdx-hox pathway, a microarray analysis was used to identify differentially expressed genes in kgg mutants and wild-type embryos. Raldh2, an enzyme required for retinoic acid (RA) production, is overexpressed in kgg mutants during the early stages of blood formation. Perz-Edwards et al., 229 Devel. Biol. 89-101 (2001); Begemann et al., 128 Devel. 3081-94 (2001). This data led to the hypothesize that RA may act to suppress blood formation and that the CDX-HOX pathway functions to limit RA production, thereby permitting blood formation to occur. In other words, the cdx-hox pathway controls retinoic acid signaling.

To test this, wild-type zebrafish embryos were treated with RA and, indeed, they became severely anemic. Treating kgg embryos with DEAB (Perz-Edwards, 2001), a chemical that blocks raldh2 activity, restored hematopoiesis in kgg mutants. Treatment with DEAB failed to rescue expression of hoxa9a, indicating that RA acts downstream of the hox genes. DEAB also induced an expansion of erythroid cells in wild-type embryos. DEAB and RA also affected the formation of mouse hematopoietic progenitors arising from ES cell-derived embryoid bodies (EBs). Addition of DEAB to EBs between days two to three of development resulted in a five-eight fold increase in 'primitive' erythroid colonies (CFU-$E^P$), analogous to results in zebrafish. Similar stimulation of primitive yolk sac erythroid cells were seen with DEAB. In contrast, RA treatment caused a general inhibition in the growth of all colony types. Taken together, these results suggest a new model in which suppression of RA by the CDX-HOX pathway is necessary for yolk sac hematopoiesis to occur. See also Davidson et al., 425 Nature 300-06 (2003); Davidson & Zon, 292(2) Devel. Biol. 506-18 (2006).

An additional gene identified is moonshine, a gene that is required for normal primitive and definitive erythropoiesis. The gene mutated is Tif1γ, a putative regulator of chromatin. Ransom et al., 2 PloS 1188-96 (2004). This factor contains a PHD finger, bromo domain, ring finger, and recently has been tied to BMP signaling through an interaction with SMAD2 and SMAD437. Dupont et al., 121 Cell 87-99 (2005). The role of this factor in hematopoiesis may be determined using suppressor enhancer screens.

An additional mutant has been designated bloodless. This gene is required for both primitive hematopoiesis and AGM hematopoiesis, although definitive hematopoiesis recovers. The bloodless phenotype appears to be non-cell autonomous and yet bloodless controls SCL and GATA1 expression. There is difficulty in mapping this mutant gene. Liao et al., 129 Devel. 649-59 (2002).

Work elucidating mechanism of erythroid to myeloid fate switch showing that GATA1 is required for suppression of the myeloid lineage. Galloway et al., 8(1) Devel. Cell 109-16 (2005). More specifically, investigating a GATA1 deficient zebrafish mutant, known as vlad tepes, and revealed that the entire blood island transformed to the myeloid fate. This interesting cell fate change illustrates that GATA1 and PU.1 antagonize each other's activity. They may form a complex that regulates the myeloid and erythroid programs. Further work demonstrated that knock-down of PU.1 changed myeloid cell progenitors into erythroid cells.39 Rhose et al., 8 Devel. Cell 97-108 (2005). This study provides a rational for plasticity within the hematopoietic system. Studying the dependency of target gene expression and of erythroid cells of GATA1 and GATA2 has shown that most genes are absolutely dependent on GATA1, yet some genes require both GATA1 and GATA2 for full expression. Several novel genes have been found that are absolutely GATA independent.

Characterization of SCL deficient morphants indicated that this SCL MO phenotype was very similar to that of the SCL knock-out in mammalian biology. SCL is required for the early hematopoietic cells to develop. Abnormal regulation of SCL is evident in both the cloche and spadetail mutants that are deficient in normal hematopoiesis. Dooley et al., 277(2) Devel. Biol. 522-36 (2005).

In an effort to understand blood island development, researchers isolated the LMO2 promoter and demonstrated that the proximal 163 base pairs of promoter are sufficient to induce GFP expression in the developing blood island as well as the vasculature. These transgenic fish lines have been invaluable for transplantation experiments. Both DsRed as well as GFP have been linked to the LMO2 promoter, allowing the construction of double transgenic lines. These LMO2 positive cells of the primitive lineage do not confer long-term reconstitution in transplantation models of early embryos or in adults. Zhu et al., 281(2) Devel. Biol. 256-269 (2005); Mead et al., 128 Devel. 2301-08 (2001); Oates et al., 98 Blood 1792-1801 (2001); Pratt et al., 11 Physiological Genomics 91-98 (2002); Huber et al., 11 Current Biology 1456-61 (2001).

A major goal was to develop hematopoietic cell transplantation for the zebrafish system. Hematopoietic population assays by flow cytometry found that simple forward scatter and side scatter can separate all the lineages of the hematopoietic system in the zebrafish. Erythroid, myeloid, and lymphoid cells could be separated as well as a precursor faction. This guided transplantation of specific cell populations into mutant embryos lacking blood. GFP positive kidney marrow from a donor was injected into these embryos that are typically bloodless. Six months after the transplant, all cells in circulation were green, indicating that they were donor-derived. The vlad tepes and bloodless embryos appeared to be excellent hosts. In addition, secondary transplants demonstrated long-term reconstituting activity in the kidney marrow. It was also demonstrated that adult marrow could be used to rescue hematopoiesis in lethally irradiated adult zebrafish. Traver et al., 104 Blood 1298-1305 (2004). This transplant protocol has been very useful for subsequent stem cell biology studies. See also Traver et al., 4 Nature Immunol. 1238-46 (2003).

Limiting-dilution analyses of zebrafish whole kidney marrow (WKM) cells may show the frequency of HSCs in zebrafish kidney marrow. Because these studies quantify the number of transplantable stem cells, they provide a functional assay for the comparison of stem cell function in wild-type versus mutant zebrafish. To this end, reconstitution studies were performed by ablating the hematolymphoid system of an unlabeled recipient using sublethal gamma-irradiation doses and then transplanting dilutions, ranging from 5,000 to 500,000, of GFP-labeled WKM cells into the host. Peripheral blood was used as carrier cells in the WKM dilution assay and served as a negative control when injected alone. After three months post-transplantation, the WKM was dissected from the hosts and analyzed by flow cytometry to measure the percentage of GFP+ donor cells in the myeloid gate. Recipients were scored as either a "success" or "failure" for donor engraftment. Using binomial maximum limits statistics, it was determined that the incidence of HSCs in zebrafish WKM is 1 in 61,910 cells with a 95% confidence interval between 50,798-79,244 cells. This number is very similar to that of a mouse, which has ~1 in 50,000 to 130,000 HSCs per bone marrow cell volume. Smith at al., 88 P.N.A.S. USA 2788-92 (1991). Therefore, these data suggest that the number of stem cells in a marrow population is evolutionarily conserved.

Work has also explored the zebrafish AGM stem cell production and the notch pathway. The AGM is thought to form from lateral mesoderm present during early somitogenesis. The tissue expresses flk1. As it migrates, it begins to express an artery specific marker called gridlock. Later, by eighteen somites, the cells express tie1 and tie2, and continue to migrate medially and form a solid cord. The cord becomes hollow and turns into the aorta. At thirty hours the runx1 transcription factor is initially expressed ventrally. Shortly after, the c-myb positive hematopoietic. cells are found in the ventral wall of the aorta. The dorsal part of the aorta expresses a T box transcription factor, called tbx20. The process in zebrafish seems very similar to that of other vertebrates including humans, mice, chickens and frogs. Galloway & Zon, 53 Curr. Topics Devel. Biol. 139-58 (2002).

The role of runx1 in the development of the AGM was also examined. Similar to the mouse knockout, a knockdown of runx1 in zebrafish led to a decreased number of cells in the AGM that are expressing c-myb. Overexpression of runx1 led to an expansion of stem cell number in the aorta, and ectopic expression of c-myb n the vein. Primitive hematopoiesis proceeds normally in the runx1 morphant. This provides evidence of a requirement of runx1 for AGM formation, and additionally establishes runx1 as a factor that is sufficient for generating definitive stem cells. Evaluation of the role of the notch pathway in AGM formation revealed that runx1 acted downstream or parallel to notch signaling.

The mutant mindbomb lacks an E3 ubiquitin ligase for delta, the ligand of notch receptors. As such, mindbomb mutants completely lack notch signaling, and fail to make any hematopoietic stem cells in the AGM. Itoh et al., 4 Devel. Cell 67-82 (2003). Overexpression of runx1 rescues the number of c-myb positive cells in the AGM in mindbomb. This implies that runx is an important target of notch. In preliminary studies, adding long-acting prostaglandin E2 to the mindbomb mutant failed to demonstrate any type of rescue. This may be due to a defect in the ability of the cells to respond to prostaglandin E2; notch signaling is likely to be required earlier in the development of the AGM region than prostaglandin E2. Dose response curves with prostaglandin E2 in the mindbomb mutant may shed light on this. Conversely, Notch ICD embryos that have increased stem cell number by 36hpf may be incubated with Cox inhibitors to see if prostaglandin signaling has a role in mediating AGM HSC upregulation. Other hematopoietic mutants may be studied similarly.

A unique transgenic system was used to examine the notch pathway. One transgenic line carrying the heat shock (HS) promoter driving gal4 was mated to another line that has UAS sequences driving the intracellular domain of notch (the activated form called NICD). Lawson et al., 128 Devel. 3675-83 (2001). This provides activated notch signal to the embryo upon heat shock. Following heat shock, the AGM of these embryos showed that c-myb and runx1 were expressed at increased intensity and over a larger area that now includes both dorsal and ventral aorta and the vein. This ectopic expression was not accompanied by a change in cell proliferation based on immunostaining with the phospho-histone H3 antibody or by BrdU labeling. This fate change could be prevented by runx1 morpholinos, formally demonstrating that runx1 acts downstream of notch.

Whether notch activation played a similar role in adult hematopoiesis was studied using the double transgenic fish to conditionally overexpress notch. Fish were sublethally irradiated with 2000 rads, and then subjected to heat shock, activating notch. Marrow hematopoiesis was analyzed by FACS for forward and side scatter, to examine myeloid, lymphoid and precursor fractions. By day seven after heat shock, the NICD expressing fish have increased myeloid and precursor fractions, and by day fourteen, there was an increase in lymphoid cells compared to wildtype. Recovery following irradiation is more rapid after notch activation. Additionally, runx1, scl and lmo2 are upregulated in adults shortly after heat shock. This confirms that the notch-runx pathway that we discovered in embryos also operates in adult zebrafish. See Burns et al., 19(19) Genes & Devel. 2331-42 (2005)

Zebrafish have also proved useful in the characterization of diseases. A number of mutant fish have been developed that have the equivalent of human disease. See, e.g. Dooley &

Zon, 10 Curr. Op. Genet. Devel. 252-56 (2000). For example, a number of membrane defects have been found in the zebrafish system that affect erythropoiesis. Among studies, mutant genes identified were BAND 3, BAND 4.1 and spectrin. Interestingly, the BAND 3 mutant appeared to have a defect that was very similar to HEMPAS or CDA type 2. BAND 3 localizes to the spindle poles in the dividing erythroid precursor where it regulates congenital; dyserthropoietic anemia. See, e.g., Liao et al., 127(3) Devel. 127(3):5123-32 (2000); Paw et al., 34(1) Nature Genet. 59-64 (2003).

Recently, grx5 was isolated as the shiraz mutant gene. Shaw et al., 440 Nature 96-100 (2006). Glutaredoxin5 is located in the mitochondria and is required for iron sulfur cluster production. The mitochondrial iron importer gene defective in the frascati mutant was also isolated, and the frascati knock-out mouse develops anemia, similar to the fish. See also Donovan et al., 403 Nature 776-81 (2000); Donovan et al., 100 Blood 4655-60 (2002); Wingert et al., 131(24) Devel. 6225-35-(2004); Fraenkel et al., 115 J. Clin. Invest. 1532-41. (2005); Wingert et al., 436 Nature 1035-39 (2005).

As part of the Trans-NIH Zebrafish Genome Initiative, an Affymetrix chip was designed. This involved investigation of over ten mutants affecting zebrafish hematopoieisis by studying gene expression patterns in mutants and wild-types at different time points. Weber et al., 106(2) Blood 521-30 (2005). We also have evaluated large-scale expression profiling by individual in situ hybridization screens have also been evaluated. This work has identified over 160 genes as part of the blood specific program.

Figure 10:
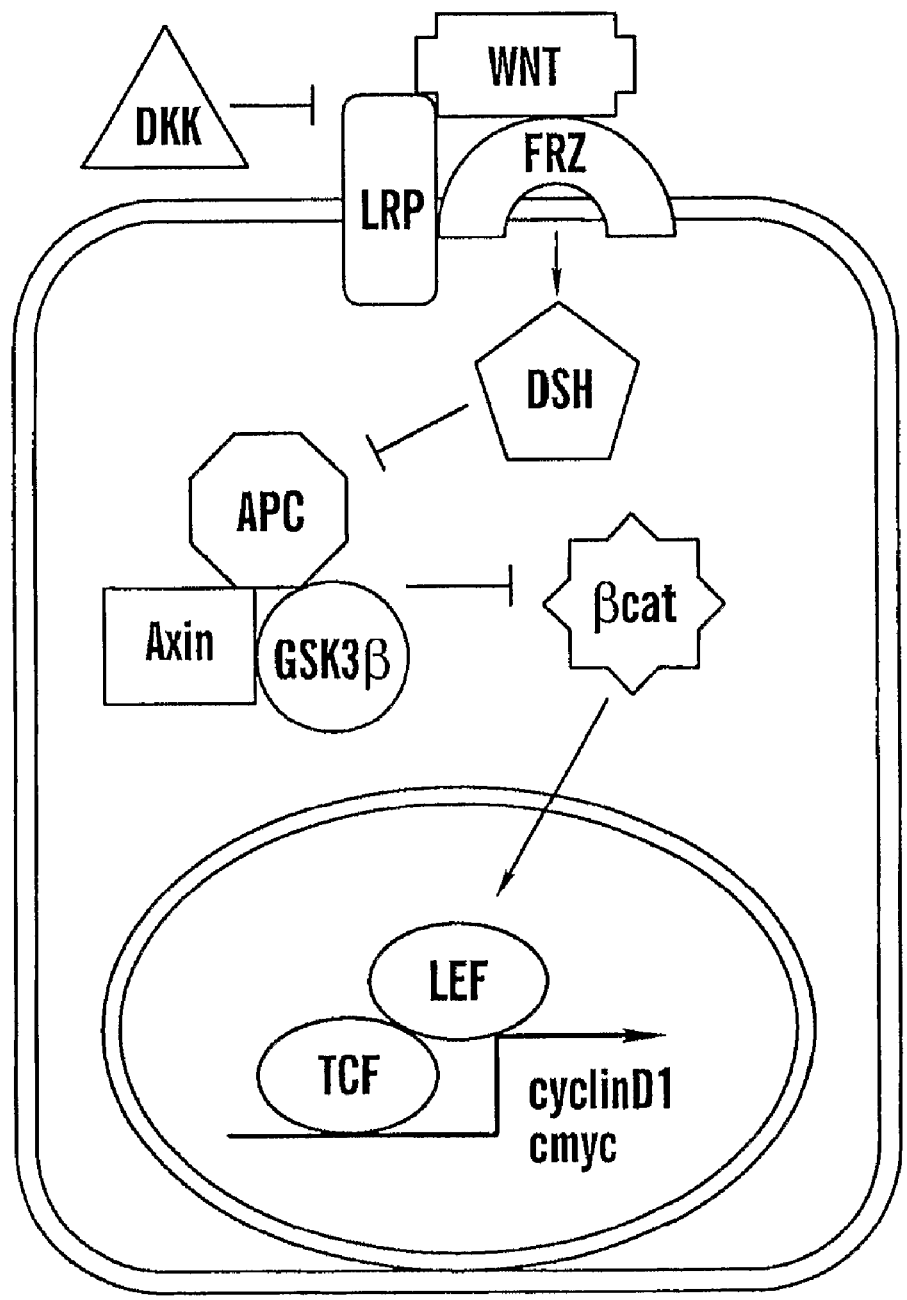
FIG. 10 presents a diagram of the Wnt signaling pathway.

The role of the wnt pathway in the formation of AGM HSCs and the potential interaction with other signaling pathways known to be active in the AGM region are also relevant. Based on elegant work on the role of the wnt pathway in HSC self renewal in adult marrow, Reya et al. 423 Nature 409-14 (2003)) the wnt pathway may regulate AGM HSC production. The canonical pathway for wnt signaling involves the activation of GSK$\beta$ and the subsequent translocation of $\beta$-catenin to the nucleus, where it then interacts with one of two similar transcription factors, TCF or LEF1 to activate wnt regulated genes (FIG. 10). The wnt pathway is negatively regulated by dickkopf and APC. The expression of wnt3 stimulates a three fold in the mouse expansion of HSCs (Reya, 2003; Wilbert et al., 423 Nature 448-52 (2003)), but surprisingly the knockout of $\beta$-catenin in HSCs does not lead to a defect in self renewal. Cobas et al., 199 J. Exp. Med. 221-29 (2004). More recent studies have demonstrated that GSK3B inhibitors lead to a reduction in HSC differentiation.

Despite what is known about the action of wnt signaling in the regulation of stem cell self-renewal, there is little information about wnt induction of definitive stem cells in the AGM. In support of the hypothesis that wnt signaling plays a role in HSC induction, $\beta$-catenin was identified through differential display RT-PCR methods as differentially expressed in the AGM region at the time of HSC formation in the mouse(REF). To define a role for wnt signaling in the AGM, the wnt pathway specific inducible lines of transgenic fish may be studied. A number of transgenic fish have been made in which the heat shock promoter drives expression of various members of the wnt pathway. Example fish for study include: heat shock wnt8, heat shock dickkopf, and heat shock dominant-negative TCF mutants. A simple pulse of heat, similar to that utilized in the notch studies, can be used to study the effect of wnt signaling inhibition or upregulation on AGM HSC production.

In an effort to better understand the role of wnt signaling in AGM formation, the heat shock wnt8 fish may be examined. wnt8 is expressed in the posterior aspect of the embryo in the tailbud region. Heat shock of the embryo between 18-22 somites led to a significant upregulation of stem cell populations in the AGM based on runx1 and c-myb expression. The activation of wnt8 leads to expansion of stem cells, but other wnts may similarly play a role in this process. It may be relevant to determine which wnt proteins are expressed in the developing AGM region. CDX4$^+$ cells will be examined by microarray analysis. Informatics may be used to examine the identity of the wnts and wnt receptors expressed in these HSCs. Additionally, wnt 3, wnt5 and wnt8 cDNAs will be studied by in situ hybridization. Other wnts deduced from the microarrays will be studied by ISH. A complete time course of heat shock during development may localize the precise period of time in which wnt signaling is required for HSC formation. The heat shock dominant negative TCF and heat shock dickkopf lines to inhibit wnt signaling in the AGM may also be examined. The dominant negative TCF eliminates the classical pathway, whereas the dickkopf heat shock construct inhibits both classical and non-classical wnt pathways. Hematopoietic stem cells were completely absent following heat exposure of these lines. To further analyze whether wnt is required for AGM HSC formation, several wnt agonist and antagonist chemicals may be tested, for example, by the methods described herein.

Gene expression studies following heat shock in the HS wnt8, HS dkk, and HS-DN TCF transgenic embryos are examined via expression hybridization techniques and Q-PCR analysis. Hematopoietic stem cell markers including SCL, LMO2, GATA-2, GATA-1, runx1, PU.1, and ikaros may be relevant to determine the effect of wnt signaling on the HSC population. Likewise the expression of markers of terminally differentiated lymphoid (rag1, LCK, immunoglobulin T cell), myeloid (myeloperoxidase, L-plastin) and erythroid (erythropoietin receptor, Erb2) blood cell populations as well as endothelial (fli1, flk1, tie2 and tie1) cells will be examined following wnt induction and inhibition. Additionally, wnt expression in the AGM region can be monitored directly using the TOP-FLASH zebrafish line. TOP-FLASH reporter fish express GFP under an inducible promoter made of multimerized LEF1 binding sites. Dorsky et al., 241 Devel. Biol. 229-37 (2002). The reporter is known to be active in posterior mesoderm formation. It is likely that cdx4, described previously, is emulated by wnt. The expression of the TOP-FLASH reporter may be examined in depth in the developing AGM region. The wnt pathway heat shock fish is useful to further investigate the role of wnt signaling in adult marrow homeostasis. Evaluating kidney marrow recovery following irradiation in the HS wnt8 and HS-DN TCF transgenic fish would decipher the requirement for wnt signaling in HSC proliferation and maintenance. In addition, limiting dilution and competitive repopulation studies with heat shock induced marrow compared to normal marrow are useful.

The relationship of the wnt and notch pathways with the prostaglandin induction of AGM stem cells may also be important in hematopoeisis. The embryonic phenotypes of notch loss of function and wnt loss of function are very similar, with both leading to a dramatic deficiency of AGM stem cells. This leads to the hypothesis that one pathway may cross regulate the other. We plan to evaluate whether the heat shock wnt8 construct will rescue the mindbomb mutant and similarly whether the dominant negative TCF mutant can be rescued by activating notch ICD. This type of analysis should lead to a better understanding of the precise timing of activation of these pathways during embryogenesis. It will also allow us to understand more about the interaction of these pathways. Mutant fish (and/or morpholino injected fish) may also be used to combine with notch and wnt deficiencies as well as gain of function phenotypes. Molecular marker examination as describe above and for Notch characterization should establish if both pathways cooperate to regulate stem cell induction and/or stem cell proliferation, renewal, and differentiation.

Members of the wnt pathway have been shown to interact with prostaglandins. For instance, for colon cancer models induced by wnt, nonsteroidals that block Cox1 or 2 prevent cancer formation. As described above, PGE2 leads to an increase in stem cells in the AGM. PGE2 may rescue wnt deficient embryos. CO inhibitor may block the effects of HS-wnt8. Other HSC modifiers encompassed by the present invention include Wnt pathway modifiers. Example Wnt pathway modifiers found to inhibit HCSs were Kenpaullone (HDAC effect, not GSK3b), and Valproic Acid (HDAC effect, not GSK3b). HSC enhancers found to modify the Wnt pathway were lithium chloride and BIO.

Using transgenic zebrafish expressing activators or repressors of wnt, the effects of wnt signaling on the development of HSCs in the aorta-gonad-mesonephros (AGM) region were examined. Induction of wnt signaling led to enhanced HSC formation, while inhibition reduced HSC production. In adult zebrafish, increased wnt activity enhanced progenitor cell number during kidney marrow recovery following irradiation. Because (PG) E2 regulates HSC formation and homeostasis in vertebrates, the interaction of the wnt and PG pathways during HSC development and in marrow recovery was explored by exposing TOP:dGFP embryos to drugs that regulate prostaglandin signaling. Dimethyl-PGE2 (dmPGE2), a potent inducer of HSC formation, was found to enhance wnt signaling, while the cyclooxygenase inhibitor indomethacin (indo), resulted in the virtual absence of wnt activity. Inhibition of HSC formation by wnt repression was partially rescued by dmPGE2 treatment, while induction of HSCs by overexpression of wnt was reversed by indo exposure. Indo also blocked the wnt-mediated increase in kidney marrow precursors following irradiation in adult fish. PGE2 induced wnt activity in the AGM of TOP:gal mice, indicating the molecular conservation of the wnt and PG interaction and the role of wnt in HSC formation.

More specifically, Wnt signaling through its main transcriptional mediator β-catenin plays an important role in controlling tissue patterning, cell fate decisions, and proliferation in many embryonic contexts, including the development and differentiation of organs. See FIG. 10. Wnt activity has been shown to increase adult HSC self-renewal and enhance stem cell repopulation following HSC transplantation into NOD/SCID mice. β-catenin was also found to be differentially expressed in the AGM regions in mouse embryos at e10-12. Whether wnt signaling has a role during HSC formation in zebrafish was determined using heat shock inducible activators and repressors of the wnt pathway. Briefly, wnt-inducible embryos were harvested and heat shocked for twenty minutes at 38° C. Genotypes were sorted by GFP expression, and the AGM HSCs analyzed by runx1/cmyb expression in situ. Induction of wnt8 by heat shock at five somites led to increased HSC formation in the AGM at 36 hpf, while abrogation of wnt signaling by induction of dkk and dnTCF significantly inhibited runx1/cmyb expression. This is the first evidence in any organism that wnt signaling is required for AGM HSC formation.

Figure 11A:
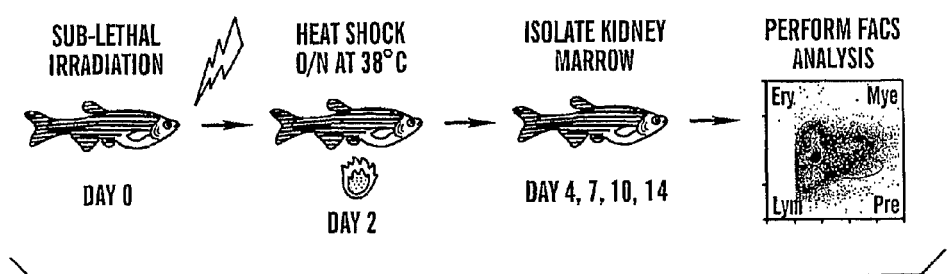
FIGS. 11A and 11B depict data that the modulation of wnt activity affects adult homeostasis.
Figure 11B:
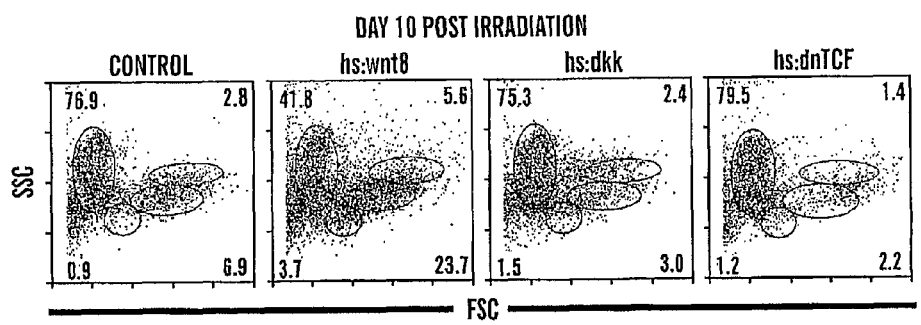

An irradiation recovery assay was also employed to investigate the role of wnt signaling in hematopoietic homeostasis in zebrafish. Transgenic fish expressing wnt-related genes were sublethally irradiated and heat shock gene induction was initiated by overnight incubation at 38° C. on day two post-irradiation. Kidney marrow was harvested at various timepoints post-irradiation as outlined previously for the prostaglandin experiments. FIG. 11. Utilizing the heat shock wnt8 fish demonstrated that an increase in the precursor population compared to controls on day ten post irradiation, similar to that seen with PGE2. Inhibition of wnt signaling, by heat shock dkk or dnTCF, drastically alters the kinetics of marrow recovery and can result in the complete failure of marrow regeneration and lethality.

Figure 12:
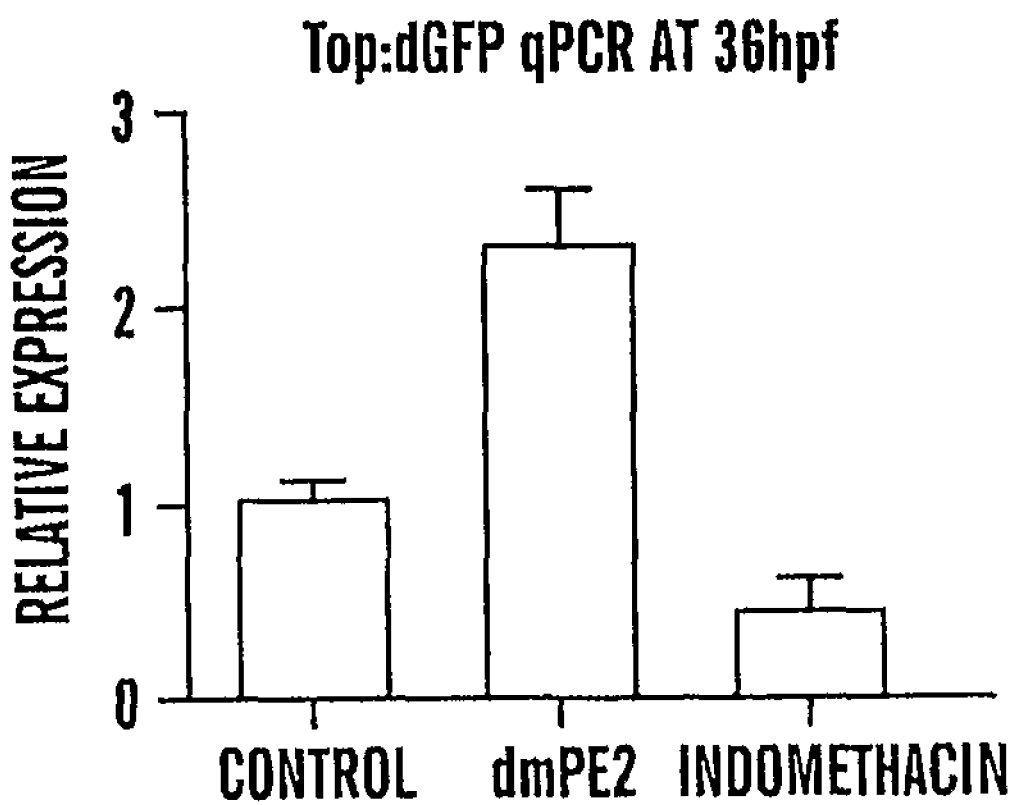
FIG. 12 shows qPCR quantification of the alterations in wnt activity in the developing embryo caused by prostaglandin signaling in an in vivo Top:dGFP assay.

Clinical experience in patients with APC mutations has shown that inhibition of prostaglandin synthesis results in decreased wnt mediated polyp formation. Furthermore, recent studies in colon cancer cell lines suggest an interaction between the prostaglandin and wnt signaling pathway. These interactions were examined in vivo using a wnt reporter zebrafish transgenic line, TOP:dGFP. At fifty-percent epiboly, embryos were subjected either to nothing (control), indomethacin, or PGE2, and the amount of wnt signaling activated in the embryo assessed by GFP induction driven from the wnt binding site. Analysis of alterations in GFP expression in the head was analyzed by in situ hybridization. Compared to the control, PGE2 treatment markedly enhanced wnt activity, while indomethacin severely reduced GFP expression. FIG. 12. These data comprise the first in vivo documentation of the interaction of the wnt and prostaglandin pathways during embryonic development.

Figure 13:
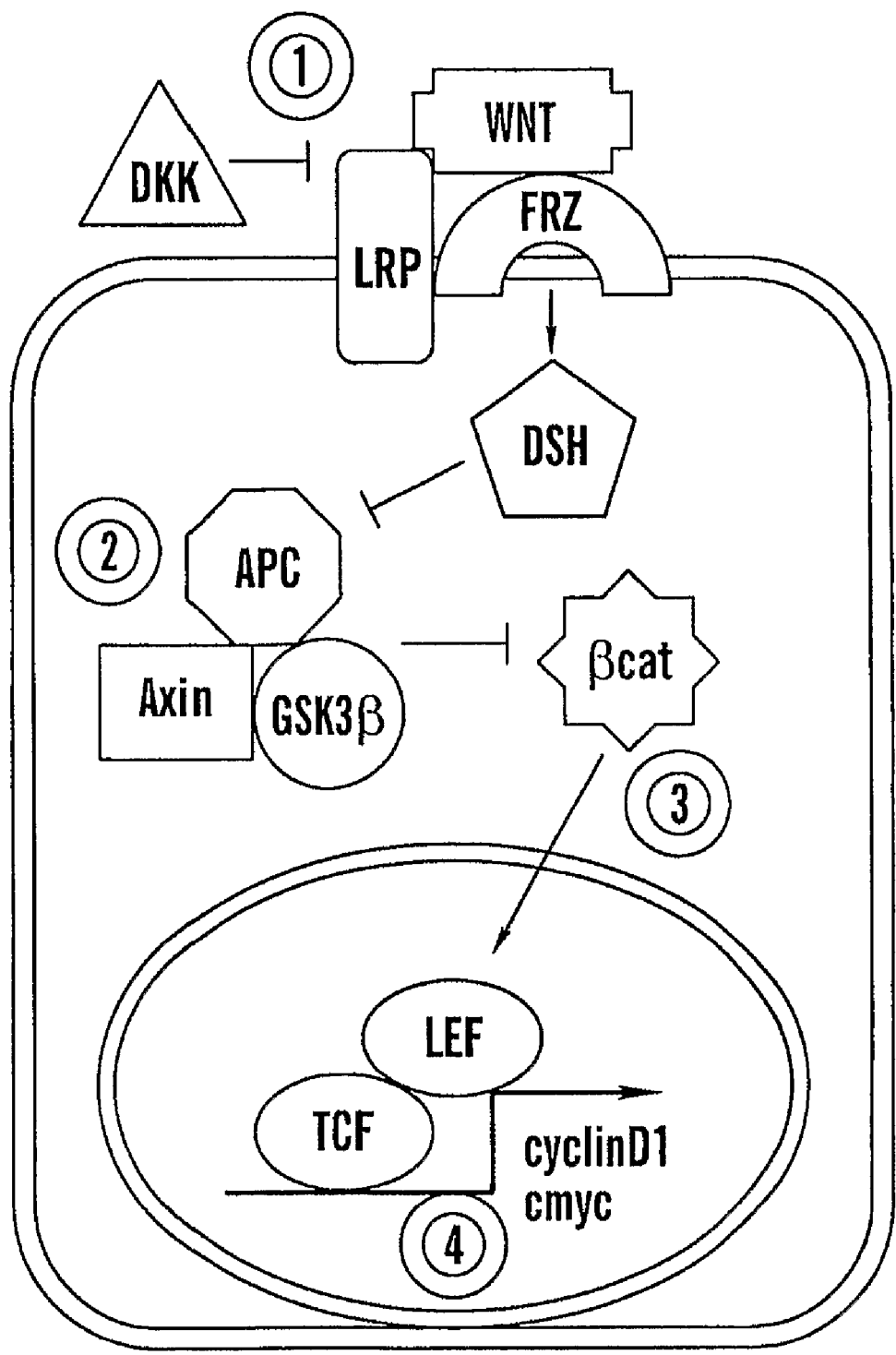
FIG. 13 presents a model depicting the potential points of interaction of the PG and wnt pathways. (1) PGE2 can not rescue dkk, axin, dnTCF; indomethacin can not block wnt8. (2) PGE2 rescues dkk, but not axin and dnTCF; indomethicin can block wnt8; PGE2 rescues dkk and axin, but not dnTCF; indomethacin can block wnt8. (4) PGE2 rescues dkk, axin and dnTCF; indomethacin can block wnt8.

Additionally, indomethacin and dmPGE2 was used to investigate the interaction of the wnt and prostaglandin pathways during HSC development and in marrow recovery following injury. FIG. 13 reflects the potential points of interaction of the PG and wnt pathways. The wnt-mediated enhancement of runx1/cmyb expression in wnt8 embryos heat shocked at five somites can be blocked by treatment with indomethacin. Furthermore, dmPGE2 can rescue the inhibitory effects of dkk activation on AGM HSC formation at 36 hpf, as shown by in situ hybridization for runx1/cmyb. Preliminary results show the dmPGE2 treatment is not sufficient, however, to rescue HSC formation in embryos over-expressing dnTCF.

Figure 14:
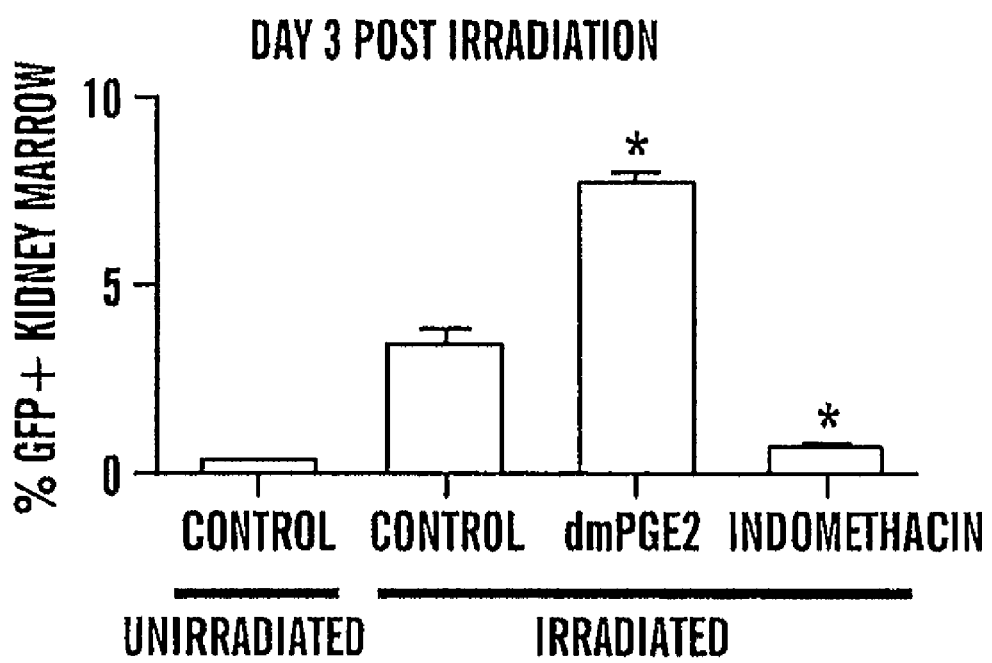
FIG. 14 shows the percent of GFP positive cells in the kidney marrow of Top:dGFP adults at day three following irradiation and treatment with dmPGE2 or indomethacin.

To determine if prostaglandin pathway manipulation can alter wnt activity in the kidney marrow repopulation in the adult, the effects of dmPGE2 and indomethacan was examined further in Top:dGFP lines. DmPGE2 significantly enhanced wnt activity on day three post irradiation, while indomethacin inhibited GFP expression. FIG. 14. To discern whether modulation of prostaglandin signaling can modify the wnt mediated effects on kidney marrow recovery following irradiation, wnt genes were activated by heat shock at 38° C. at two days post irradiation and then. exposure to prostaglandin pathway drugs at one day post heat shock. The hs:wnt8-GFP fish were exposed to indomethacin, while the dkk1, axin, and dnTCF transgenic fish were exposed to dmPGE2. Whole kidney marrow was analyzed by FACS on day ten post-irradiation. Treatment with indomethacin was observed to severely diminish the wnt-mediated enhancement in the precursor cell population, suggesting that PGE2 levels can directly modulate wnt-signaling in vivo.

These experiments suggest that pharmacological manipulation of wnt activity through modulation of PG signaling will provide a novel means for therapeutically regulating HSC homeostasis.

Several embodiments will now be described further by non-limiting examples.

EXAMPLES

Example 1

Chemical Screen Design and Confirmatory Testing

Wild-type age-matched embryos were arrayed into 48-well plates (~5 embryos/well) of individual test compounds and exposed from 3-somites until 36 hpf. Three compound libraries were utilized: NINDS Custom Collection (1040), SpecPlus Collection (960) and BIOMOL ICCB Known Bioactives (480). Five percent (123/2480) of the compounds were toxic, resulting in death or severe morphological abnormalities. In situ hybridization for runx1 and cmyb was performed to assess HSCs. Compounds were retested at 10 µM, 20 µM, and 50 µM. Stem cell specificity was assessed using flk1 at 36hpf. PGE2, PGI2, dmPGE2 and all cox inhibitors (Sigma) were used at 10 µM to 20 µM.

Qualitative scoring (# embryos with altered HSCs/# scored) of runx1/cmyb was conducted using the following criteria: Normal/unchanged=continuous line of runx1/cmyb$^+$ endothelial cells and occasional hematopoietic clusters. Decreased/absent=reduction in runx1/cmyb$^+$ cells, including the presence of large gaps in the line of HSCs, isolated positive cells, or absence of expression. Increased/excess=enhancement in runx1/cmyb$^+$ cells, including many HSC clusters, a thickened line of HSCs, or ectopic expression.

Confocal Imaging

Live 36 hpf treated bigenic zebrafish embryos were embedded in 1% low-melting point agarose containing 0.4 mg/ml Tricaine-S for confocal imaging. cmyb-GFP transgenic reporter lines were created from a BAC containing the cmyb promoter genomic sequence (Galloway, Zhu, Lin, Zon, unpublished); lmo2:DsRed fish were created as described[27]. For HSC quantification, cmyb/lmo2+ positive cells were counted in projections of z-stack images (n=10/treatment).

Morpholino Knockdown

Morpholino oligonucleotides (GeneTools) directed against zebrafish cox1 and cox2, PGE2 synthase, and EP2 and EP4 (Grosser et al., 2002; Cha et al., 2006, Pina et al., 25 Arterioscler. Thromb. Vasc. Biol. 315-20 (2005)), were injected (40 µM) into zebrafish embryos at the one-cell stage. For rescue experiments, 3-somite stage MO-injected embryos were exposed to 10 µM dmPGE2.

Microarray Gene Expression Profiling gata1:GFP (12 somites), lmo2:GFP (12 somites and 35 hpf) and cd41:GFP (35 hpf) positive cells were FACS-sorted; total RNA was purified and analyzed using Affymetrix zebrafish gene chips as described previously. Weber et al., 106 Blood 521-30 (2005).

Quantitative PCR qPCR was performed using previously described primer sets. Burns et al., 19 Genet Devel. 2331-42 (2005). Embryos (n=50) were treated as described. qPCR (60° C. annealing) was performed using SYBR Green Supermix on the iQ5 Multicolor RTPCR Detection System (BioRad) (n=10 replicates) and relative expression levels were determined. Primer pairs for EP2 and EP4 were determined by methods well known in the art. qPCR of whole KM RNA (n=15/variable) was performed on day three post-irradiation as described. Burns et al., 19 Genes Devel. 2331-42 (2005). qPCR on S cell RNA (harvested in Stat-60, Tel-Test) was performed using the Stratagene Sybrgreen kit on the Stratagene qPCR machine. PG primer sequences were determined by methods well known in the art.

Mass Spectroscopy

PGE$_2$ and the stable PGI$_2$ metabolite, 6-keto-PGF$_{1\alpha}$, were measured using HPLC-tandem mass spectrometry. Ethylacetate extracts from homogenized embryos were spiked with the corresponding stable isotope labeled internal standards (d$_4$-PGE$_2$ and d$_4$-6-keto PGF$_{1\alpha}$) and allowed to react with methoxylamine. The following mass transitions were monitored: m/z 384→272 (PGE), m/z 398→368 (6-keto PGF$_{1\alpha}$ and TxB2).

Radiation Recovery Assay

Adult zebrafish were exposed to 23 Gy of γ-irradiation. On day two post-irradiation, fish were exposed overnight to DMSO control, dmPGE2 (10 or 50 µM), Indomethacin (10 µM), SC560 (10 µM) or NS398 (10 µM) in fish water. Whole KM isolated on days 0, 2, 4, 7, 10, 14 was subjected to FSC/SSC FACS analysis to identify hematopoietic lineages (n=5/treatment×3 replicates). Traver et al., 104 Blood 12980305 (2004).

ES Cell Differentiation Assays

ES cell hematopoietic differentiation assays were performed as previously described. Kyba et al. 100(1) P.N.A.S. USA 11904-10 (2003); Wang et al., 102 P.N.A.S. USA 19081-86 (2005). dmPGE2 (10, 20 or 100 µM) or indomethacin (20, 100 µM) were added at day four and day five during EB expansion. M3434 methylcellulose colony forming and OP9 colony assays were conducted on day 6 and analyzed at days 8 and 5, respectively. Colony type was identified by morphological analysis; duplicate chemical exposures were averaged to determine the reported colony number (n=3 replicates minimum).

Murine Colony-Forming Units-Spleen (CFU-S)

WBM cells from the femurs of 8-week old C57B1/6 mice were incubated ex vivo with (1 µM/106 cells) dmPGE2, indomethacin, SC560, NS398 or EtOH control on ice for two hours. Two independent BM samples were treated (n=5/treatment×2 replicates) for each variable. Recipient mice were lethally irradiated with a split dose of 10 Gy. 6×10$^4$ unfractionated dmPGE2 or control-treated BM cells were injected retro-orbitally into irradiated recipient mice. Spleens were dissected on day eight or twelve, weighed and fixed with Bouin's solution; hematopoietic colonies per spleen were counted. 1×10$^5$ cells/recipient were transplanted after treatment with the cox inhibitors. FACS sorted ckit$^+$sca1$^+$lineage$^-$ BM cells were treated as above and transplanted at a dose of either 100 cells/recipient or 300 cells/recipient.

5-Fluorouracil Bone Marrow Injury

Mice were treated with 5-FU (150 mg/kg) as described. Venezia et al., 2004. SC560, NS398, dmPGE2 (1 mg/kg) or EtOH control were administered by IP injection on days 1, 5, 9, 13, and 17 post injection. Peripheral blood was obtained on day seven and day fourteen, quantified and subjected to multilineage FACS analysis using antibodies (eBioscience) to B220/IgM (B-lymphoid), CD4/8 (T-lymphoid), Mac1/Gr1 (myeloid), Ter119/CD71 (erythroid) and ckit/sca1 (stem/progenitor). Mice were sacrificed on day 16, and bone marrow was isolated, quantified and analyzed by FACS.

Limiting Dilution Competitive Transplantation

WBM from CD45.1 C57B1/6 mice was incubated with dmPGE2 or EtOH control ex vivo as described. Treated-test cells were independently transplanted into irradiated CD45.2 recipients (n=5/variable×2) with untreated CD45.1/CD45.2 competitor at the following ratios: 15,000:200,000 (0.075:1), 50,000:200,000 (0.25:1), 200,000:200,000 (1:1), 2,000,000: 200,000 (10:1). Peripheral blood (PB) was obtained at six, twelve, and twenty-four weeks post-transplantation, and white blood cells were FACS-analyzed to determine test reconstitution for each series of treatment populations. Frequency of PB chimerism >5% was used to calculate the number of repopulating cells using the L-Calc program (Stem Cell Technologies). For twelve-week and twenty-four-week PB samples, multilineage reconstitution was measured by FACS analysis as above.

Example 2

Additional HSC Modulators

Zebrafish embryos were screened as described above. Another group of HSC modifiers identified by the techniques described herein and encompassed by the present invention are cAMP/P13K/AKT second messenger modifiers, which may be downstream of PG signaling. Those which inhibit HCS include PD9805, KT5720, H89, U0126, and Wortmannin. Those which enhance HSC include 8-bromo-cAMP and Forskolin.

Another group of HSC modifiers that may also act downstream of PG signaling are Ca2+ second messenger modifiers. These include HSC inhibitors and HSC enhancers listed in Table 9:

TABLE 9

Example Ca2+ second messenger modifiers

| HSC Inhibitors | HSC Enhancers |
| --- | --- |
| BayK 8644 | Bapta-AM |
| Thioridazine | Fendiline |
|  | Nicardipine |
|  | Pimozide |
|  | Strophanthidin |
|  | Lanatoside |

A further group of HSC modifiers identified by the screening techniques described herein and encompassed by the present invention are NO/Angiotensin signaling modifiers, which may interact with PG and wnt signaling. These include HSC inhibitors and HSC enhancers listed in Table 10:

TABLE 10

Example NO/Angiotensin signaling modifiers

| HSC Inhibitors | HSC Enhancers |
| --- | --- |
| L-NAME | L-Arg |
| Enalapril | Sodium Nitroprusside |
| Captopril | Sodium Vanadate |
| AcSDKP | Bradykinin |
| Losartan |  |
| Telimasartan |  |
| Histamine |  |
| Ambroxol |  |
| Chrysin |  |
| Cycloheximide |  |
| Methylene Blue |  |
| Epinephrine |  |
| Dexamethazone |  |
| Proadifen |  |
| Benzyl isothiocyanate |  |
| Ephedrine |  |

The zebrafish screening methods of the present invention were also applied to identify other HSC modulators whose interactions with PG or wnt signaling are presently unclear. These compounds, also encompassed by the present invention, include those with either inhibit or enhance HCSs as indicated in Table 11:

TABLE 11

Example HSC modulators.

| HSC Inhibitors | HSC Enhancers |
| --- | --- |
| Paragyline | Mebeverine |
| Propranolol | Flurandrenolide |
| Etanidazole | Atenolol |
| Methimazole | Pindolol |
| Cinoxacin | Gaboxadol |
| Penicillamine | Kynurenic Acid |
| Furosemide | Hydralazine |
| Eburnamininone | Thiabendazole |
| Aclarubicin | Bicuclline |
| Warfarin | Vesamicol |
| Gamma-aminobutyric Acid | Peruvoside |
| Norethindrone | Imipramine |
| Lupinidine | Chlorpropamide |
| Hydroquinidine | 1,5-Pentamethylenetetrazole |
| Todralazine | 4-Aminopyridine |
| Methoxamine | Diazoxide |
| Hydroxyurea | Benfotiamine |
| Dihydroergotamine | 12-Methoxydodecenoic acid |
| Antazoline | N-Formyl-Met-Leu-Phe |
| 3-Nitropropionic Acid | Gallamine |
| N-Phenylanthranilic Acid | IAA 94 |
| Phenazopyridine | Chlorotrianisene |
| Dichlorokynurenic acid |  |
| 3-estradiol |  |
| L-Leu |  |
| Phenoxybenzamine |  |
| Mephentermine |  |
| Guvacine |  |
| Guaiazulene |  |
| Imidazole |  |
| Beta-Carotene |  |
| Clofibrate |  |

The invention claimed is:

1. A method for promoting hematopoietic stem cell (HSC) engraftment in a human subject, comprising contacting a population of human HSCs ex vivo with 16,16-dimethyl-PGE$_2$ to promote engraftment of the HSC in the subject and administering the contacted HSCs to the subject, wherein the population of HSCs is obtained from peripheral blood, cord blood, bone marrow, amniotic fluid, or placental blood.

2. The method of claim 1, wherein the population of cells is cryopreserved.

3. The method of claim 1, wherein the subject is a candidate for bone marrow or stem cell transplantation, or a subject that has received bone marrow ablating chemotherapy or irradiation therapy.

* * * * *

UNITED STATES PATENT AND TRADEMARK OFFICE
CERTIFICATE OF CORRECTION

| | | |
|---|---|---|
| PATENT NO. | : 8,168,428 B2 | Page 1 of 1 |
| APPLICATION NO. | : 12/294344 | |
| DATED | : May 1, 2012 | |
| INVENTOR(S) | : Leonard I. Zon et al. | |

It is certified that error appears in the above-identified patent and that said Letters Patent is hereby corrected as shown below:

In the Specification

Please substitute the Government Support paragraph (Column 1, lines 17-19) with the following:

> This invention was made with Government support under Grant Nos. CA103846-02 and DK071940 awarded by the National Institutes of Health. The Government has certain rights in this invention.

Signed and Sealed this
Twenty-sixth Day of May, 2015

Michelle K. Lee
*Director of the United States Patent and Trademark Office*